United States Patent
Nelson et al.

(10) Patent No.: US 7,958,895 B2
(45) Date of Patent: *Jun. 14, 2011

(54) MAGNETIC FORCE DEVICES, SYSTEMS, AND METHODS FOR RESISTING TISSUE COLLAPSE WITHIN THE PHARYNGEAL CONDUIT

(75) Inventors: Lionel M. Nelson, Los Altos, CA (US); Ronald G. Lax, Tarpon Springs, FL (US); Eric N. Doelling, Sunnyvale, CA (US); Jinfang Liu, Lancaster, PA (US); Peter H. Muller, Woodside, CA (US); Ryan P. Boucher, San Francisco, CA (US); Michael L. Reo, Redwood City, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1217 days.

This patent is subject to a terminal disclaimer.

(21) Appl. No.: 11/638,229

(22) Filed: Dec. 13, 2006

(65) Prior Publication Data
US 2007/0089756 A1    Apr. 26, 2007

Related U.S. Application Data

(62) Division of application No. 10/656,861, filed on Sep. 6, 2003, now Pat. No. 7,188,627.

(60) Provisional application No. 60/441,639, filed on Jan. 22, 2003, provisional application No. 60/456,164, filed on Mar. 20, 2003.

(51) Int. Cl.
*A61B 19/00* (2006.01)
*A61F 5/56* (2006.01)

(52) U.S. Cl. ........... 128/897; 128/848
(58) Field of Classification Search ............ 600/9–15; 128/897–898, 846, 848, 859; 623/9, 11.11, 623/14.11
See application file for complete search history.

(56) References Cited

U.S. PATENT DOCUMENTS

| | | |
|---|---|---|
| 4,304,227 A | 12/1981 | Samelson |
| 4,978,323 A | 12/1990 | Freedman |
| 5,019,372 A | 5/1991 | Folkman et al. |
| 5,176,618 A | 1/1993 | Freedman |
| 5,220,918 A | 6/1993 | Heide et al. |
| 5,373,859 A | 12/1994 | Forney |
| 5,465,734 A | 11/1995 | Alvarez et al. |
| 5,792,067 A | 8/1998 | Karell |
| RE36,120 E | 3/1999 | Karell |
| 5,988,171 A | 11/1999 | Sohn |
| 6,231,496 B1 | 5/2001 | Wilk |
| 6,244,865 B1 | 6/2001 | Nelson et al. |
| 6,250,307 B1 | 6/2001 | Conrad et al. |
| 6,390,096 B1 | 5/2002 | Conrad et al. |
| 6,401,717 B1 | 6/2002 | Conrad et al. |
| 6,408,851 B1 | 6/2002 | Karell |
| 6,415,796 B1 | 7/2002 | Conrad et al. |
| 6,450,169 B1 | 9/2002 | Conrad et al. |
| 6,490,885 B1 | 12/2002 | Wilkinson |
| 6,523,541 B2 | 2/2003 | Knudson |

(Continued)

FOREIGN PATENT DOCUMENTS
DE    43 07 262    9/1994

*Primary Examiner* — John P Lacyk

(57) ABSTRACT

Devices, systems and methods employ magnetic force to resist tissue collapse in targeted pharyngeal structures and individual anatomic components within the pharyngeal conduit during sleep.

11 Claims, 27 Drawing Sheets

U.S. PATENT DOCUMENTS

| | | |
|---|---|---|
| 6,636,767 B1 | 10/2003 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,188,627 B2 * | 3/2007 | Nelson et al. ......... 128/898 |
| 7,481,224 B2 * | 1/2009 | Nelson et al. ......... 128/897 |
| 7,500,484 B2 * | 3/2009 | Nelson et al. ......... 128/897 |
| 2001/0047805 A1 | 12/2001 | Scarberry et al. |
| 2004/0112390 A1 | 6/2004 | Brooks et al. |
| 2005/0092332 A1 | 5/2005 | Conrad et al. |

\* cited by examiner

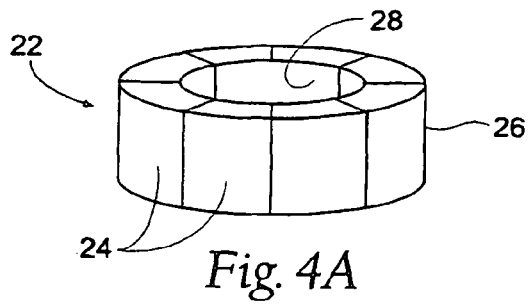
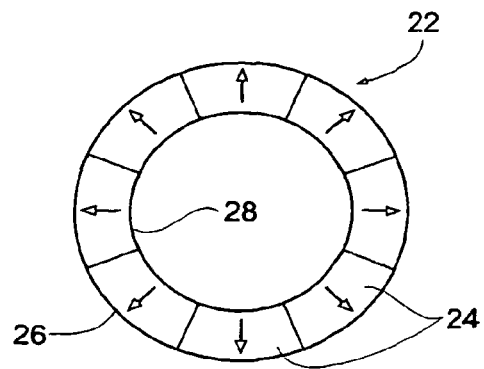
Fig. 4A
Fig. 4B
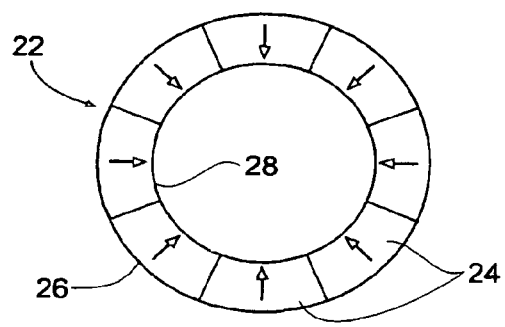
Fig. 4C
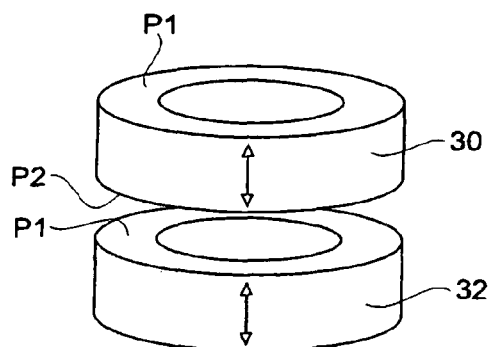
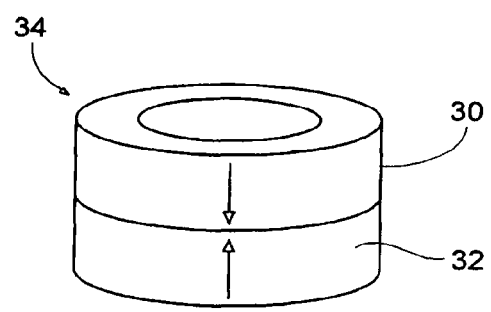
Fig. 5A
Fig. 5B
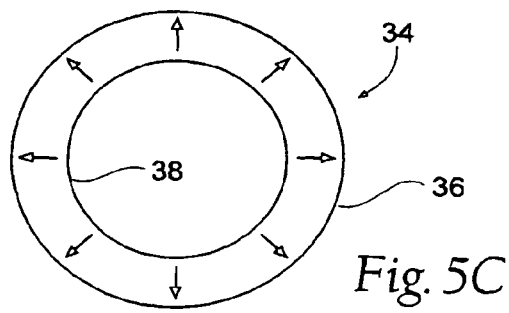
Fig. 5C

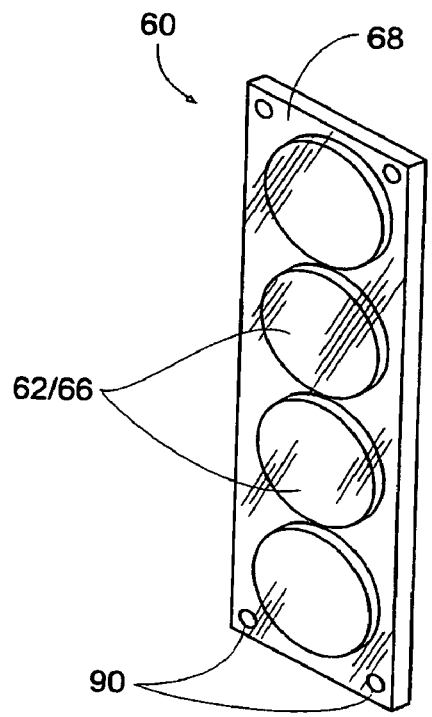
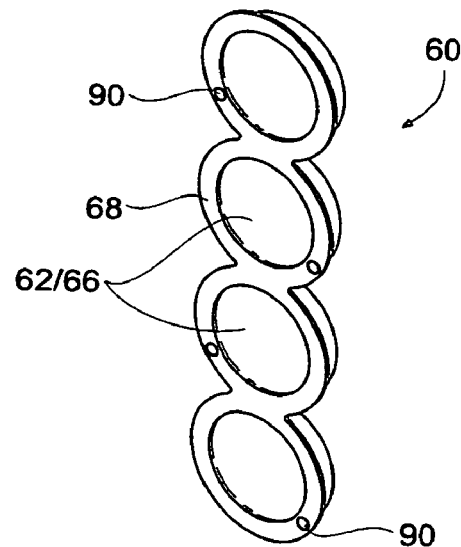
Fig. 10A    Fig. 10B
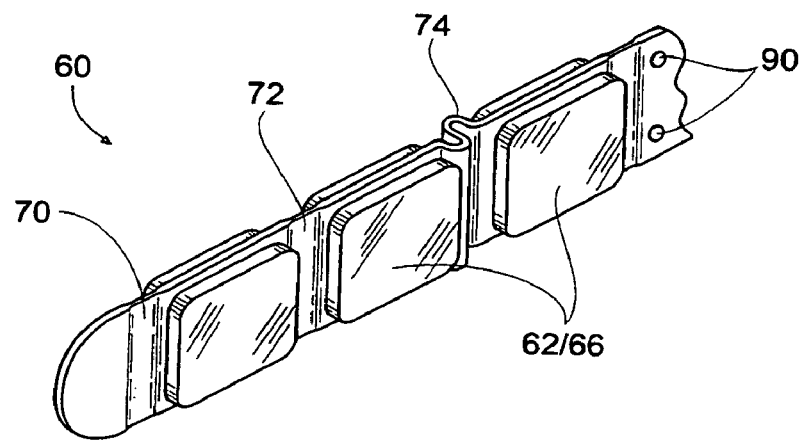
Fig. 11

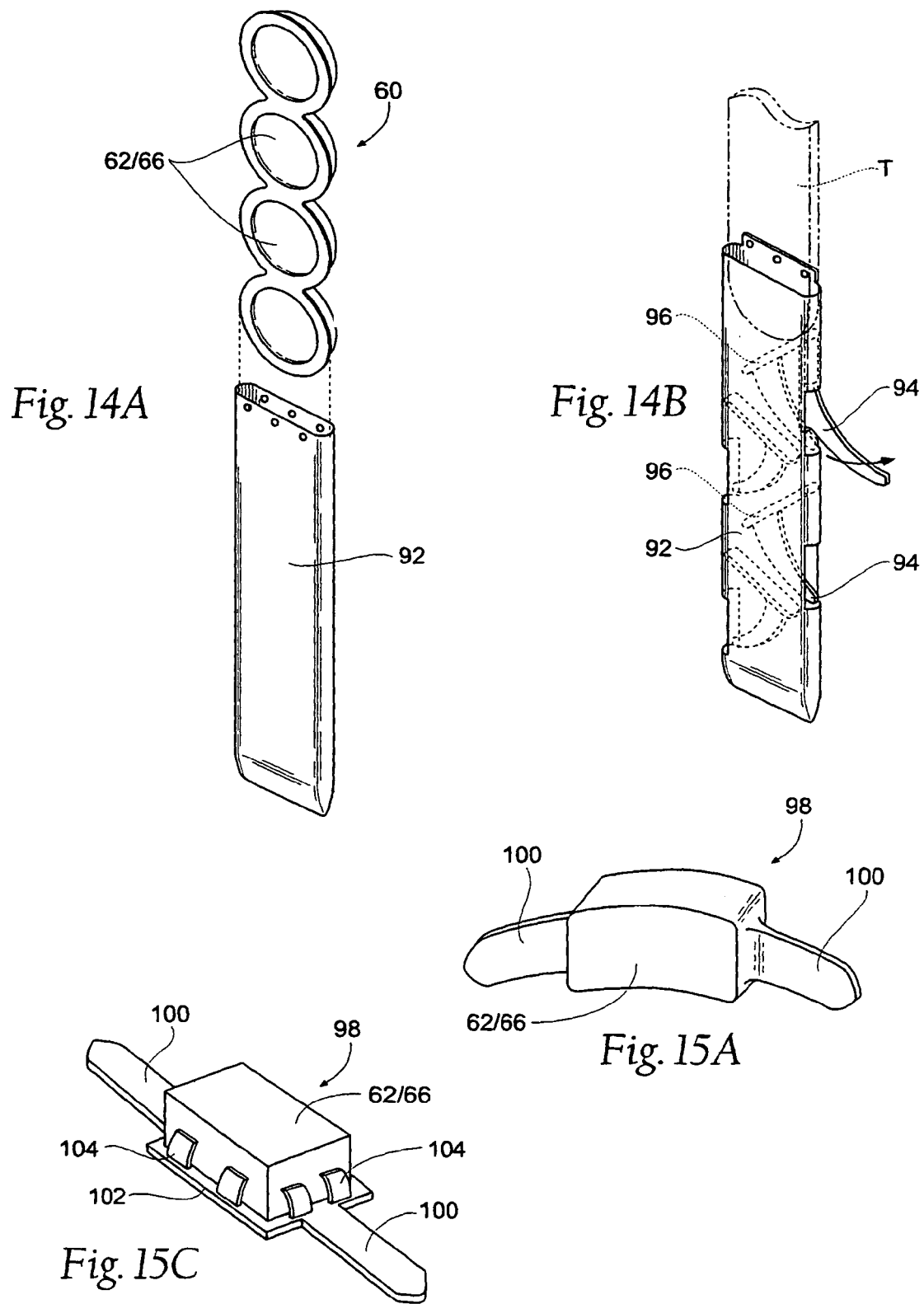

MAGNETIC FORCE DEVICES, SYSTEMS, AND METHODS FOR RESISTING TISSUE COLLAPSE WITHIN THE PHARYNGEAL CONDUIT

RELATED APPLICATIONS

This application is a divisional of U.S. patent application Ser. No. 10/656,861, filed Sep. 6, 2003, now U.S. Pat. No. 7,188,627, and entitled "Magnetic Force Devices, Systems, and Methods for Resisting Tissue Collapse within the Pharyngeal Conduit," which claims the benefit of U.S. patent application Ser. No. 10/236,455, filed Sep. 6, 2002 and entitled "Systems and Methods for Moving and/or Restraining Tissue in the Upper Respiratory System"; and U.S. Provisional Patent Application Ser. No. 60/441,639, filed Jan. 22, 2003 and entitled "Magnetic Splint Device and Method for the Treatment of Upper Airway Collapse in Obstructive Sleep Apnea;" and U.S. Provisional Patent Application Ser. No. 60/456,164, filed Mar. 20, 2003 and entitled "Device and Method for Treatment of Sleep Related Breathing Disorders Including Snoring and Sleep Apnea," which are each incorporated herein by reference.

FIELD OF THE INVENTION

The invention is directed to devices, systems, and methods for the treatment of sleep disordered breathing including obstructive sleep apnea.

BACKGROUND OF THE INVENTION

I. The Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. It is one of the several entities that make up the broader group of sleep disordered breathing (SDB). This group of disorders ranges from habitual snoring to OSA. Normally, the muscles of the upper part of the throat keep the airway open to permit air flow into the lungs. When the muscles of the upper airway relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" can be quite frequent. These breathing pauses are almost always accompanied by snoring between apnea episodes, although not everyone who snores has OSA.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all humans, the frequency of blockages will determine the seriousness of the disease and opportunity for health damage. When the incidence of blockage is frequent, corrective action should be taken.

II. Sleep and the Anatomy of the Upper Airway

As FIGS. 1A and 1B show, the upper airway consists of a conduit that begins at the nasal valve, situated in the tip of the nose, and extends to the larynx. Although all tissue along this conduit is dynamic and responsive to the respiratory cycle, only the pharyngeal conduit structures—the tissues in the region of the airway that starts behind the nasal cavity and ends in its connections to the supraglottic larynx—is totally collapsible. The pharyngeal structures and individual anatomic components within this region include the pharyngeal walls; the base of the tongue; the vallecula; the hyoid bone and its attachments; the soft palate with uvula, the palatine tonsils with associated pillar tissue; and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. Schwab R J, Goldberg A N. *Upper Airway Assessment: Radiographic and other Imaging Techniques. Otolaryngol Clin North Am* 1998; 31:931-968.

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx. Isono S. Remmers J, Tanaka A Sho Y, Sato J, Nishino T. *Anatomy of Pharynx in Patients with Obstructive Sleep Apnea and in Normal Subjects. J Appl Physiol* 1997: 82:1319-1326.

Although anatomic closure is often accentuated at specific sites, such as the velopharyngeal level [Isono, Ibid], studies of closing pressures [Isono, Ibid] supports dynamic fast MRI imaging that shows narrowing and collapse usually occurs along the entire length of the pharynx. Shellock F G, Schatz C J, Julien P, Silverman J M, Steinberg F, Foo T K F, Hopp M L, Westbrook P R. *Occlusion and Narrowing of the Pharyngeal Airway in Obstructive Sleep Apnea: Evaluation by Ultrafast Spoiled GRASS MR Imaging. Am J of Roentgenology* 1992: 158:1019-1024.

III. Prior Treatment Modalities

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid-vallecula levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

The use of magnetic energy to prevent closure of the airway has previously been proposed. Freedman U.S. Pat. No. 5,176, 618. Freedman's proposal does not address the lateral pharyngeal wall or the placement of arrays of magnets affecting larger areas of the pharyngeal conduit.

The need remains for simple, cost-effective devices, systems, and methods for reducing or preventing sleep disordered breathing events.

SUMMARY OF THE INVENTION

The invention provides devices, systems and methods that employ magnetic force to resist tissue collapse in targeted pharyngeal structures and individual anatomic components within the pharyngeal conduit during sleep.

One aspect of the invention provides systems and methods that comprise a first magnetically interactive material sized and configured for placement in or on a tongue, and a second magnetically interactive material sized and configured for placement in a desired relationship with the tongue to magnetically interact with the first magnetically interactive material by repelling the first magnetically interactive material to stabilized a preferred orientation of the tongue.

Other features and advantages of the invention shall be apparent based upon the accompanying description, drawings, and claims.

DESCRIPTION OF THE DRAWINGS

FIG. 1B is a superior view taken generally along line 1B-1B in FIG. 1.

FIGS. 4A, 4B, and 4C are illustrative types of cylindrical permanent magnet assemblies having radial magnetization that can be used as an implanted ferromagnetic material and/or a source of magnetic force in the system 10 shown in FIG. 2.

FIGS. 5A, 5B, 5C, 5D, 5E, and 5F are illustrative types of permanent magnets comprising axially magnetized permanent ring magnets that, when assembled, have radial magnetization that can be used as an implanted ferromagnetic material and/or a source of magnetic force in the system 10 shown in FIG. 2.

Figure 2:
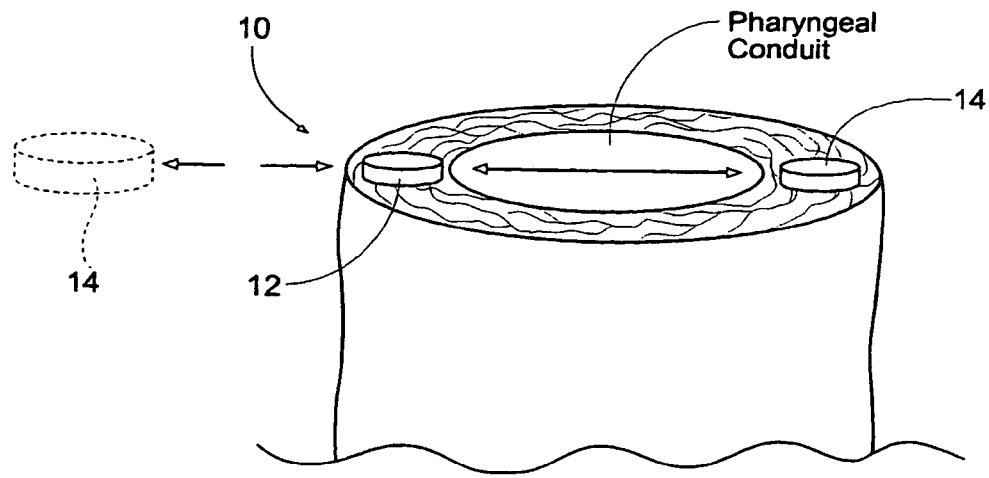
FIG. 2 shows in a diagrammatic way a magnetic force system 10 comprising an implanted ferromagnetic material 12 and a source magnetic force that interact to resist the collapse of tissue in targeted pharyngeal structures and individual anatomic components within the pharyngeal conduit during sleep.
Figure 8:
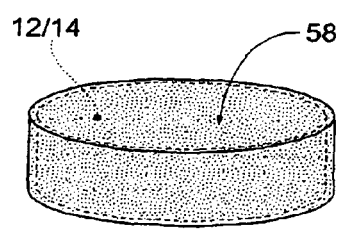

As FIG. 8 shows a ferromagnetic material usable with the system 10 shown in FIG. 2 that is enclosed within a selected protective material 58, providing a biocompatible, durable, corrosion-resistant interface with tissue/fluids of the body.

Figure 9A:
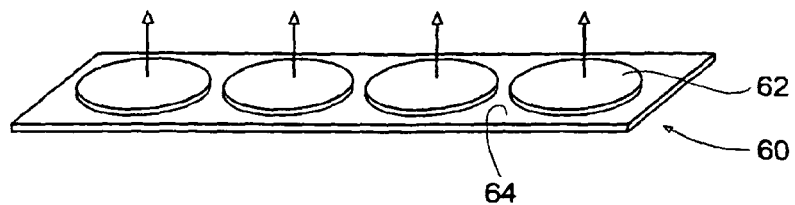
Figure 9B:
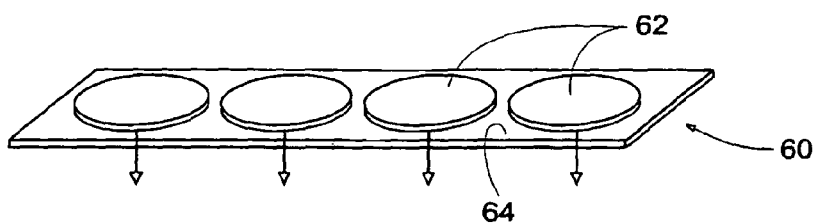
Figure 9C:
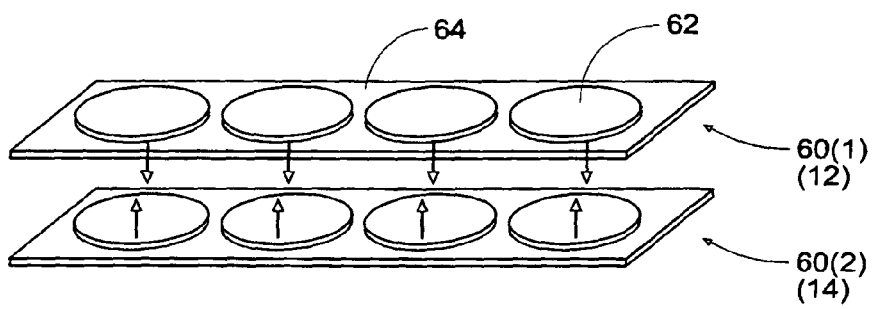
Figure 9D:
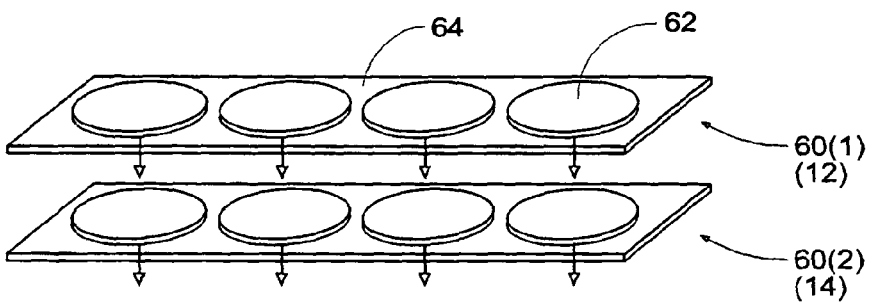
Figure 9E:
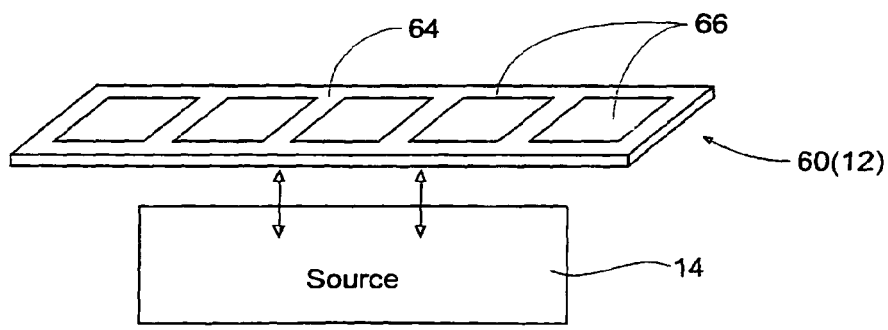

FIGS. 9A, 9B, 9C, 9D, and 9E show flexible magnetic arrays that can be used in the system 10 shown in FIG. 2 to provide either a repelling magnetic field (e.g., FIG. 9C) or an attracting magnetic field (e.g., FIGS. 9D and 9E).

FIGS. 10A and 10B show one illustrative embodiment of a flexible magnetic array that can be used in the system 10 shown in FIG. 2 to provide either a repelling magnetic field or an attracting magnetic field.

Figure 12:
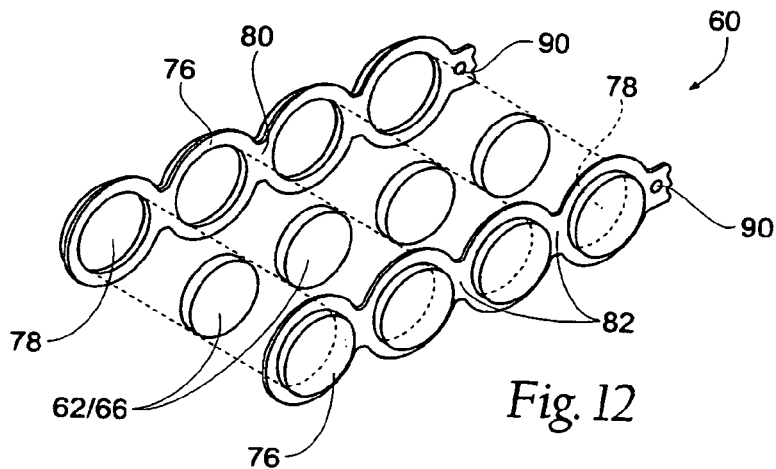

FIGS. 11 and 12 show illustrative embodiments of flexible magnetic arrays that can be used in the system 10 shown in FIG. 2 to provide either a repelling magnetic field or an attracting magnetic field.

Figure 13A:
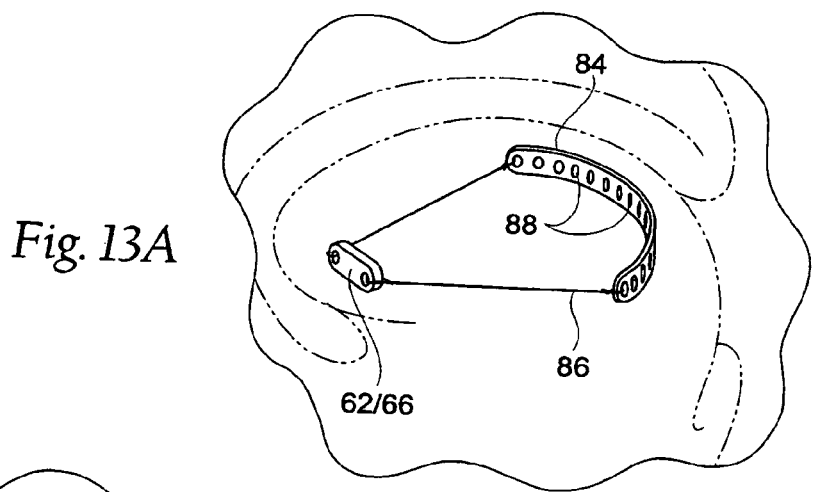
Figure 13B:
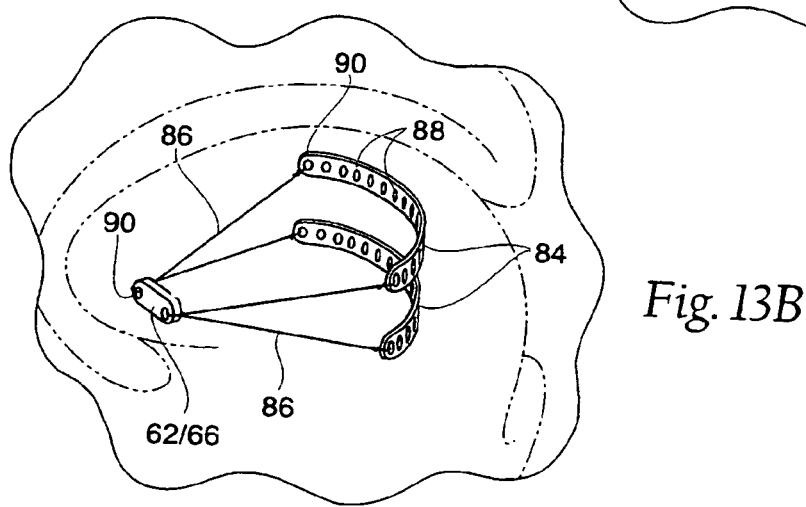

FIGS. 13A and 13B shows a permanent magnet or soft ferromagnetic material tethered by suture or a band to at least one holding or anchoring structure, which can be used in the system 10 shown in FIG. 2.

FIGS. 14A and 14B show a sleeve that receives a single magnet or soft ferromagnetic material, or an array of magnets or soft ferromagnetic materials, for implantation to form a system 10 shown in FIG. 2.

Figure 15B:
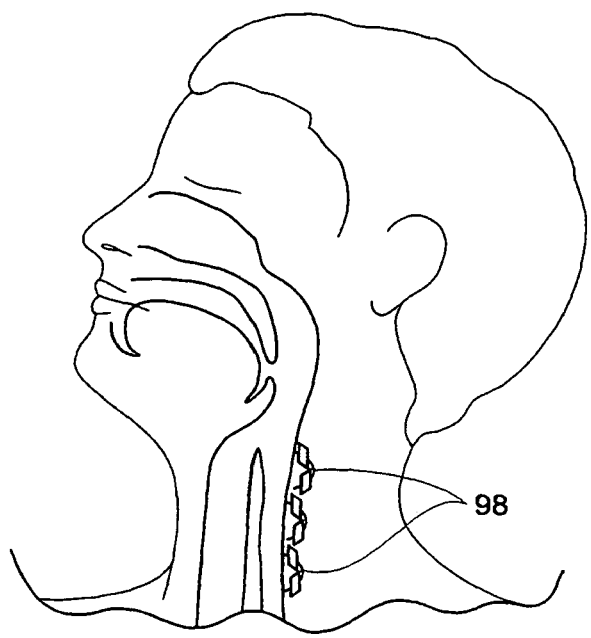

FIGS. 15A, 15B, and 15C show a magnet-staple assembly, which can be used in the system 10 shown in FIG. 2.

Figure 16:
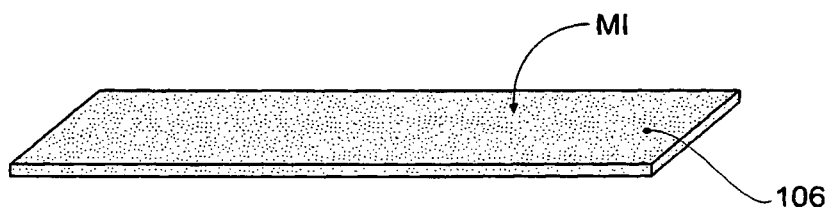

FIG. 16 shows a magnetic implant having a tissue in-growth surface 106, which can be used in the system 10 shown in FIG. 2.

Figure 17A:
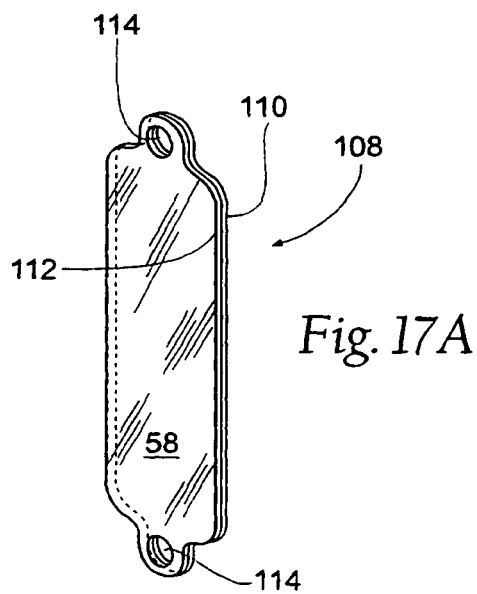
Figure 17C:
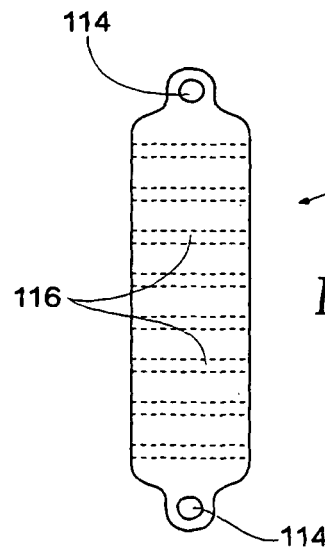
Figure 17B:
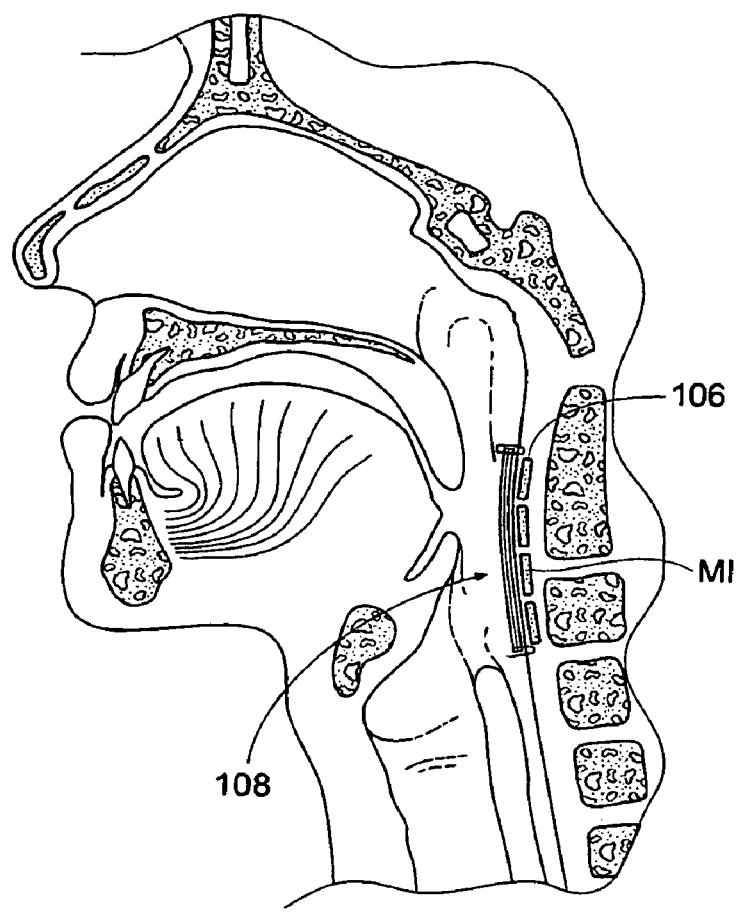

FIGS. 17A, 17B, and 17C show a shunt device made of soft ferromagnetic materials that can be used in association with the magnetic implant shown in FIG. 16 to reduce the magnetic flux field while tissue in-growth proceeds.

Figure 18A:
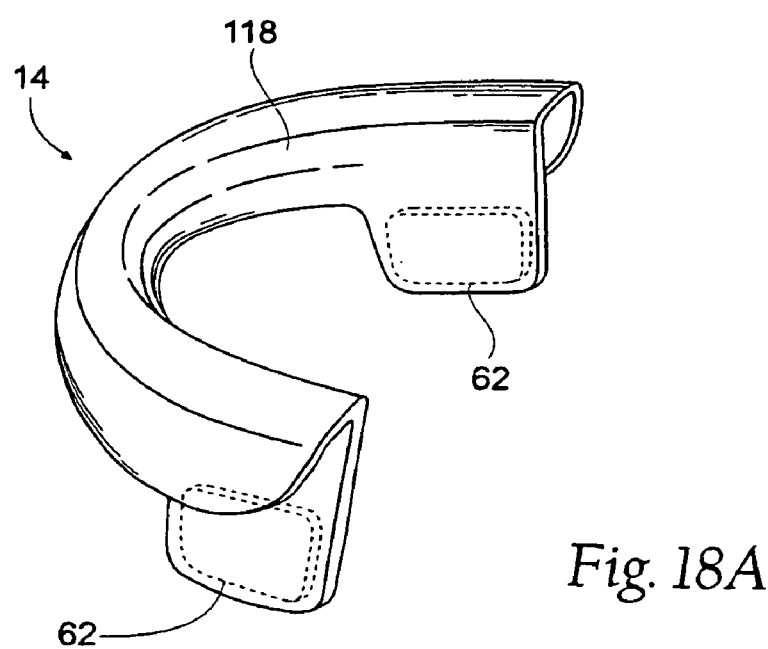
Figure 18B:
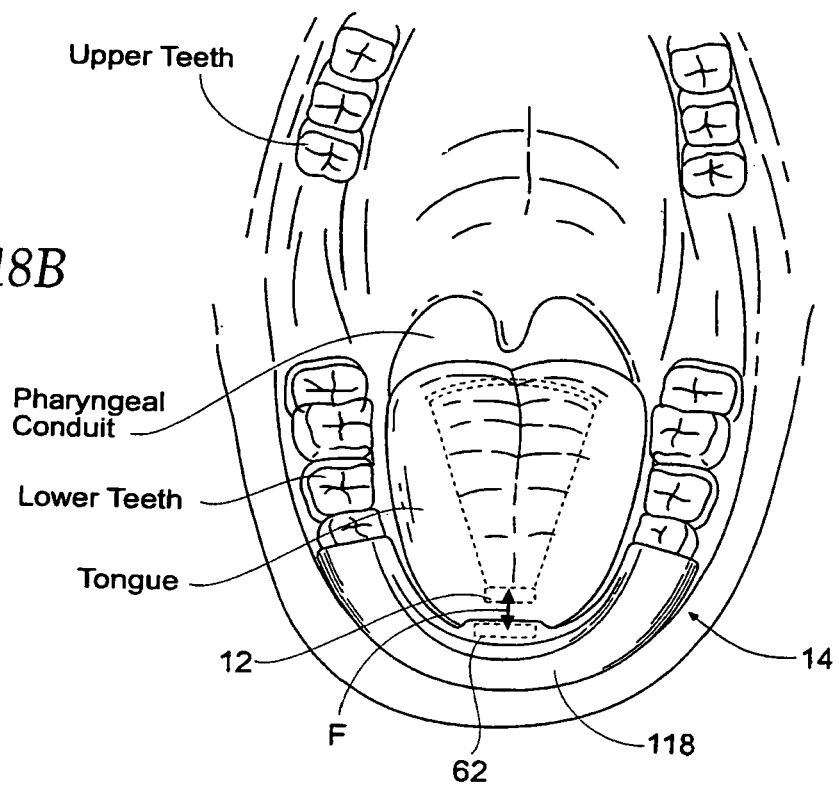
Figure 18C:
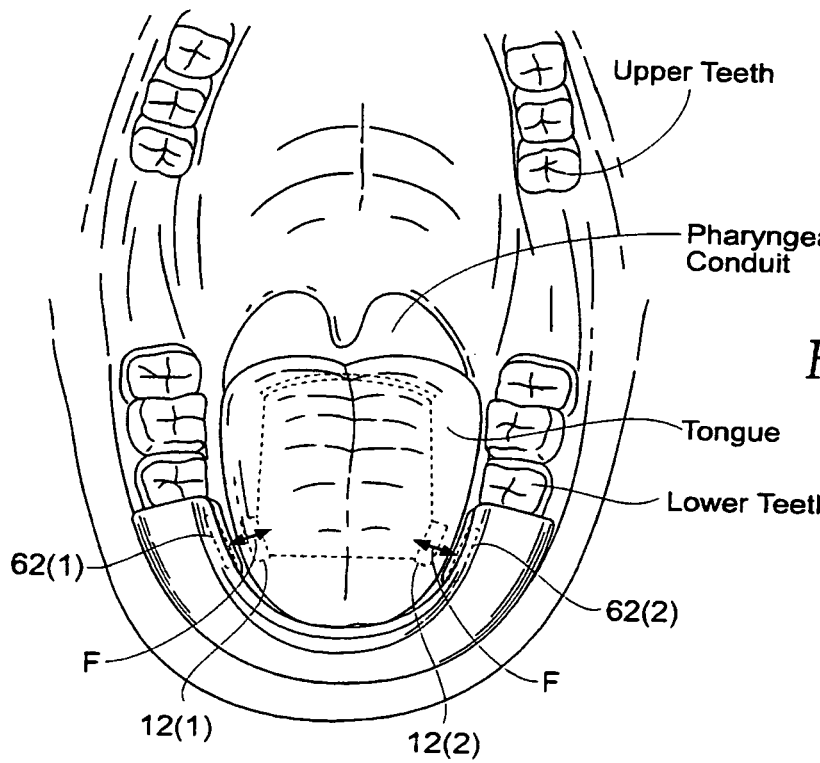

FIGS. 18A, 18B, and 18C show a magnetic force source carried by an oral appliance sized and configured to be worn on the lower teeth, which can be used to generate an attracting magnetic field interacting with ferromagnetic material of either soft magnetic material or a permanent magnet with unlike magnetic orientation implanted in the tongue, comprising a system 10 shown in FIG. 2.

Figure 19A:
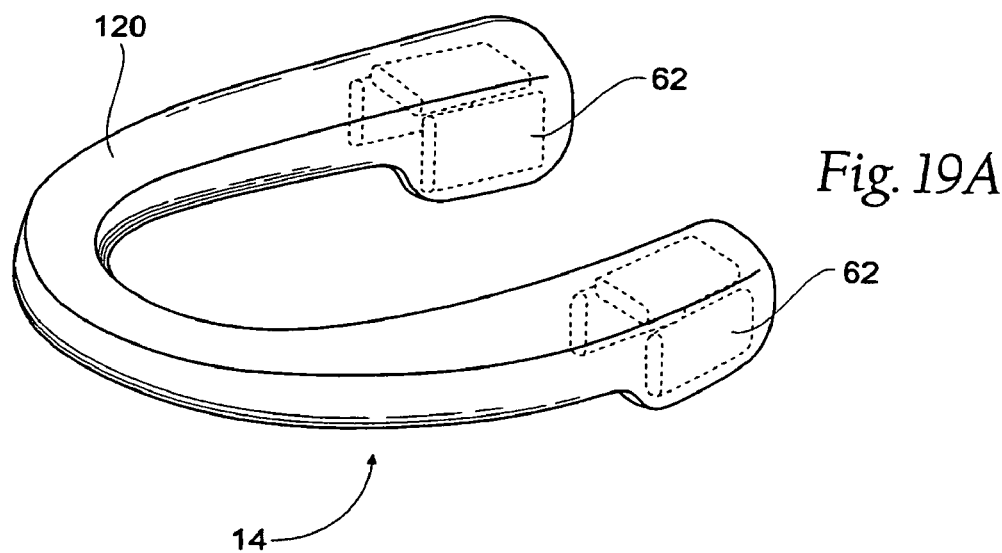
Figure 19B:
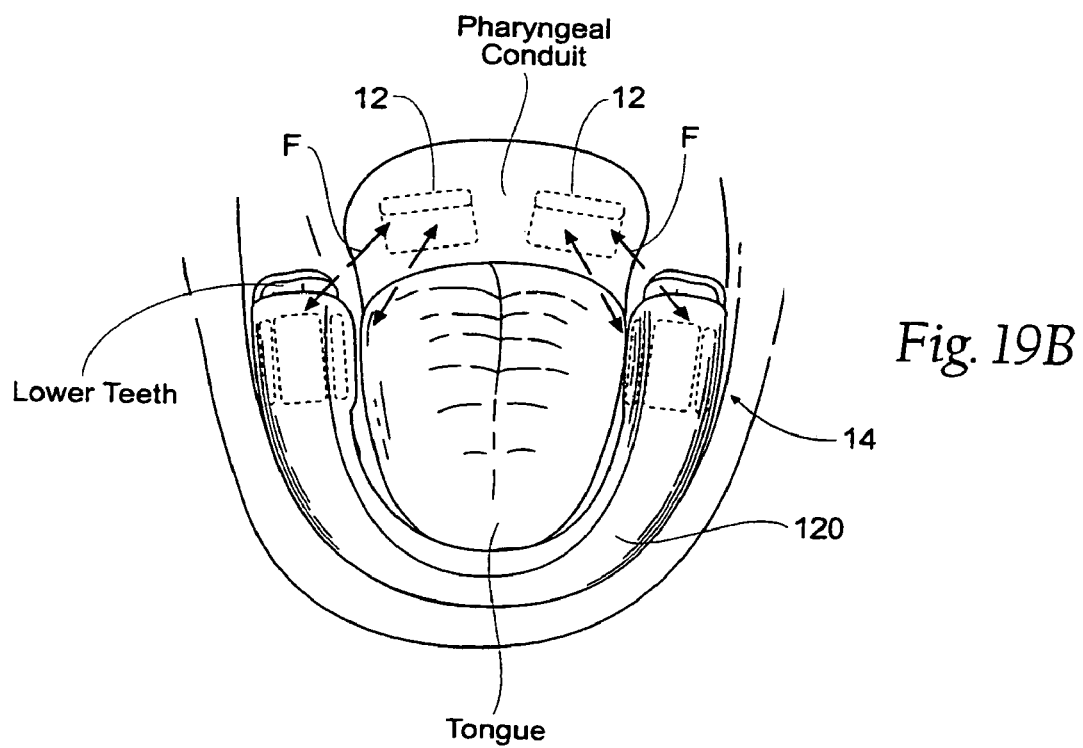

FIGS. 19A and 19B show a magnetic force source carried by an oral appliance sized and configured to be worn on the lower teeth, which can be used to generate a repelling magnetic field interacting with ferromagnetic material implanted in the pharyngeal wall, comprising a system 10 shown in FIG. 2.

Figure 20A:
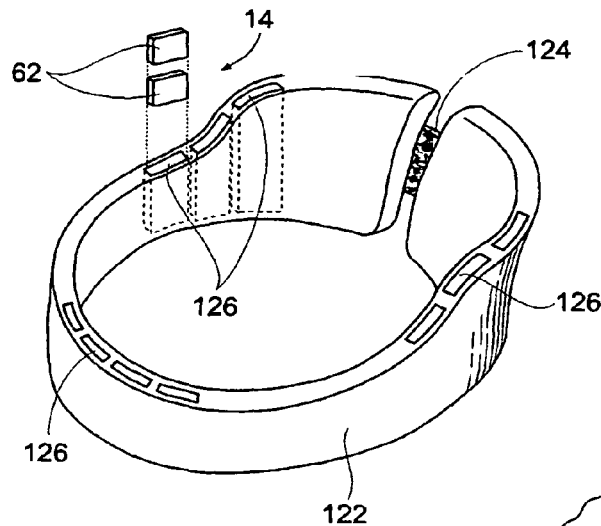
Figure 20B:
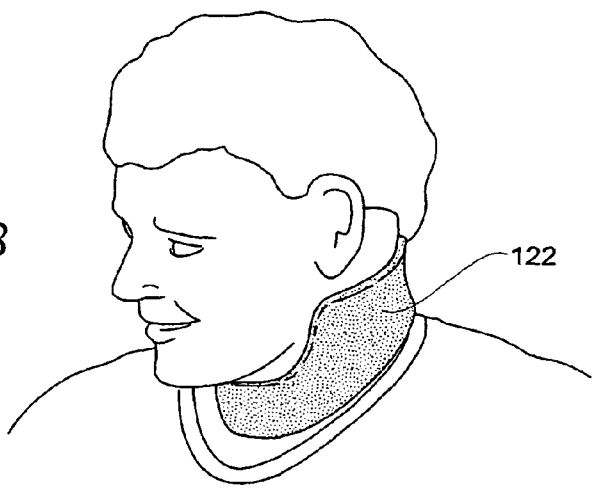
Figure 20C:
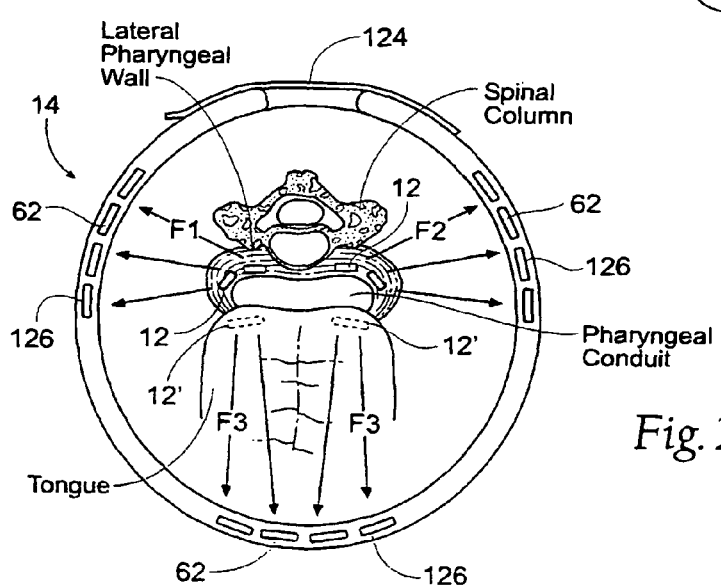

FIGS. 20A, 20B, and 20C show a magnetic force source carried by a neck appliance, which can be used to generate an attracting magnetic field interacting with ferromagnetic material of either soft magnetic material or a permanent magnet with unlike magnetic orientation implanted in the tongue and/or pharyngeal wall, comprising a system 10 shown in FIG. 2.

Figure 21A:
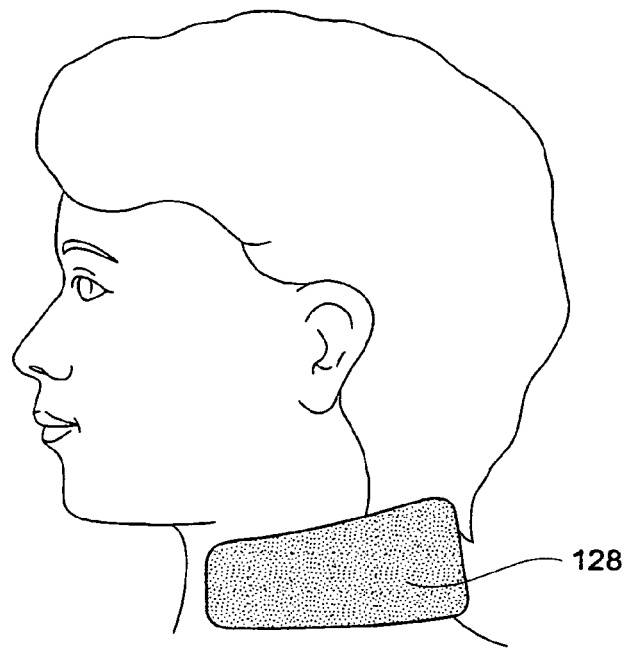
Figure 21B:
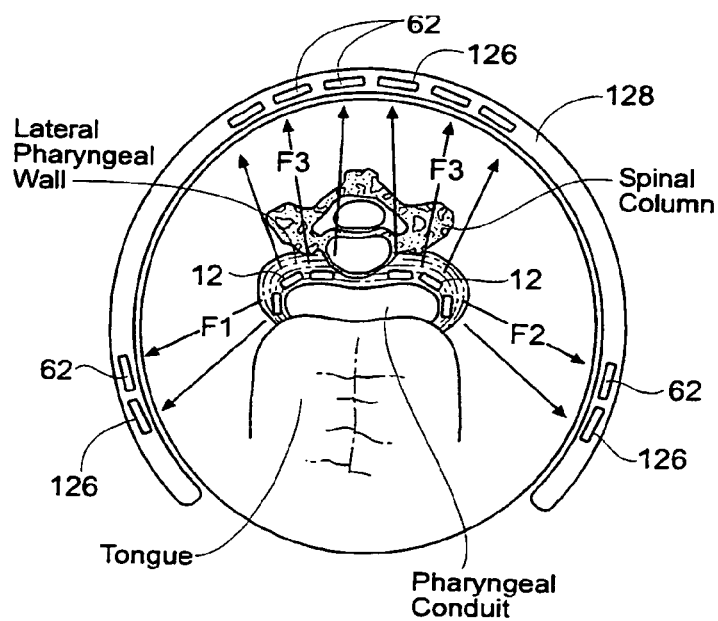

FIGS. 21A and 21B show a magnetic force source carried by another type of neck appliance, which can be used to generate an attracting magnetic field interacting with ferromagnetic material of either soft magnetic material or a permanent magnet with unlike magnetic orientation implanted in the pharyngeal wall, comprising a system 10 shown in FIG. 2.

Figure 22A:
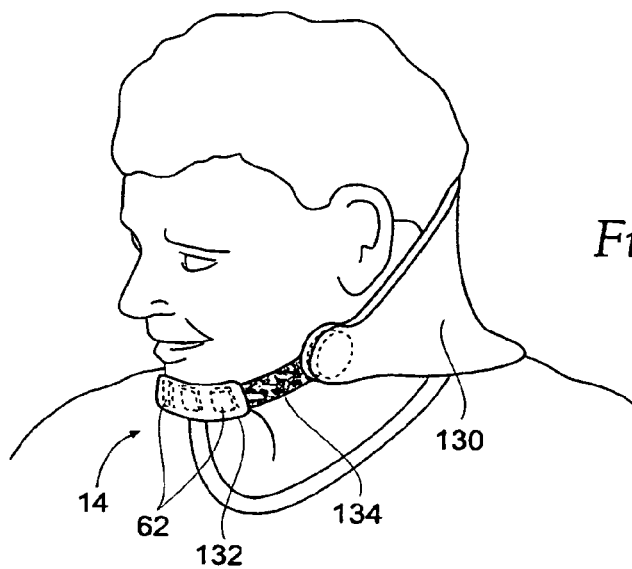
Figure 22B:
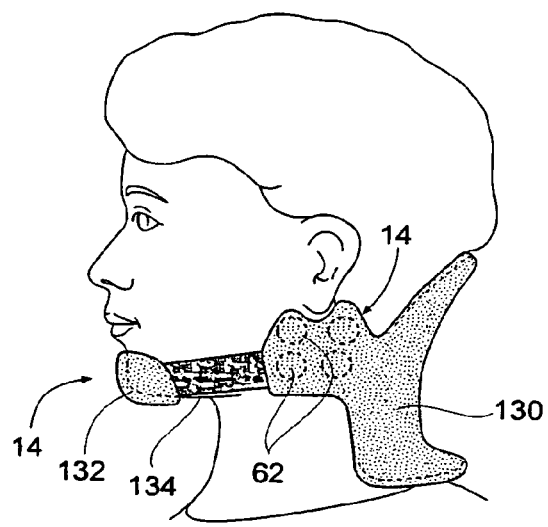
Figure 22C:
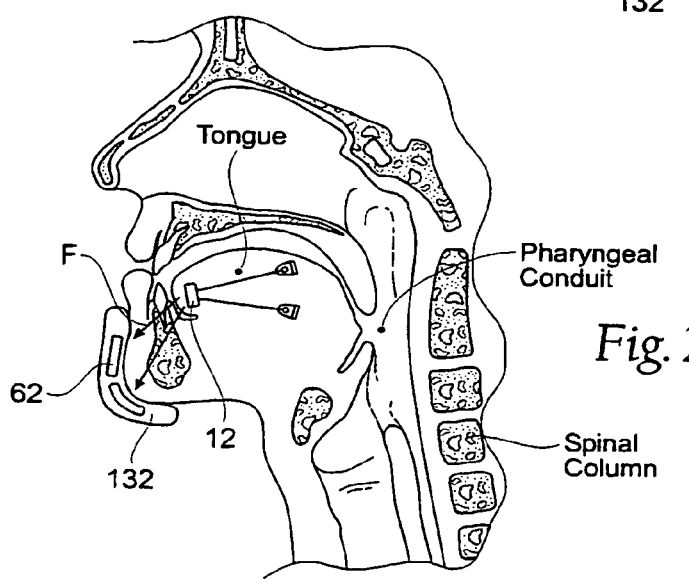

FIGS. 22A, 22B, and 22C show a magnetic force source carried by another type of neck appliance, which can be used to generate an attracting magnetic field interacting with ferromagnetic material of either soft magnetic material or a permanent magnet with unlike magnetic orientation implanted in the tongue and/or pharyngeal wall, comprising a system 10 shown in FIG. 2.

Figure 23A:
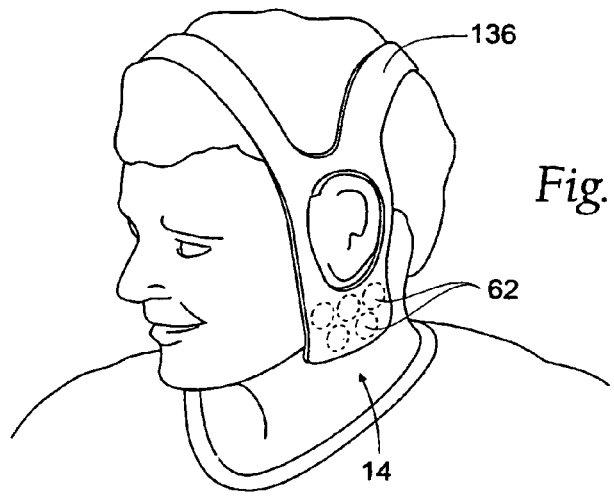
Figure 23B:
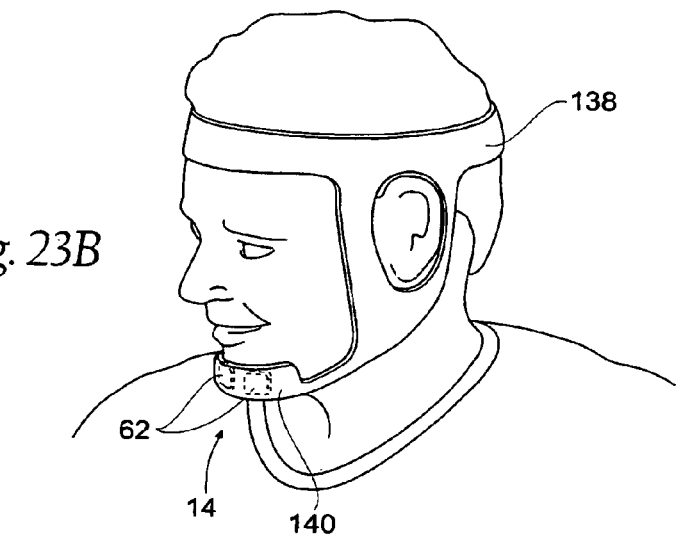
Figure 23C:
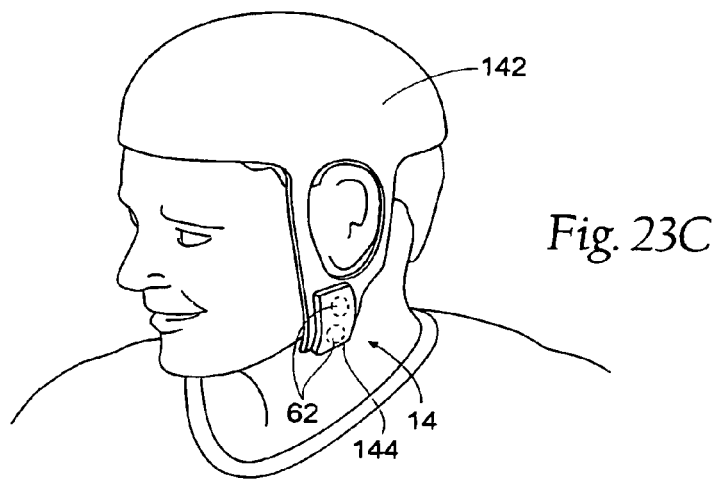

FIGS. 23A, 23B, and 23C show a magnetic force source carried by various types of headgear, which can be used to generate an attracting magnetic field interacting with ferromagnetic material of either soft magnetic material or a permanent magnet with unlike magnetic orientation implanted in the tongue and/or pharyngeal wall, comprising a system 10 shown in FIG. 2.

Figure 24A:
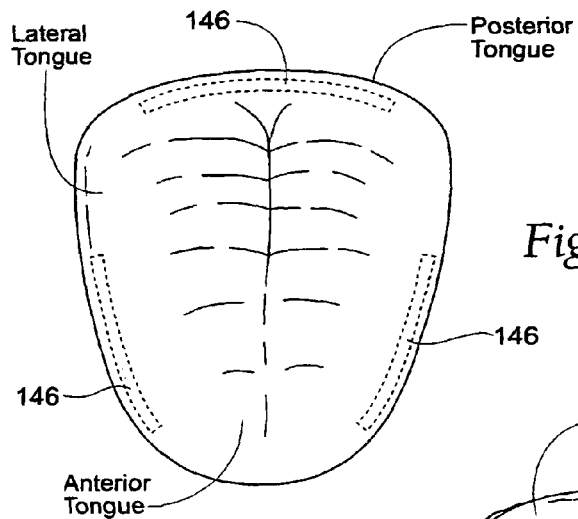
Figure 24B:
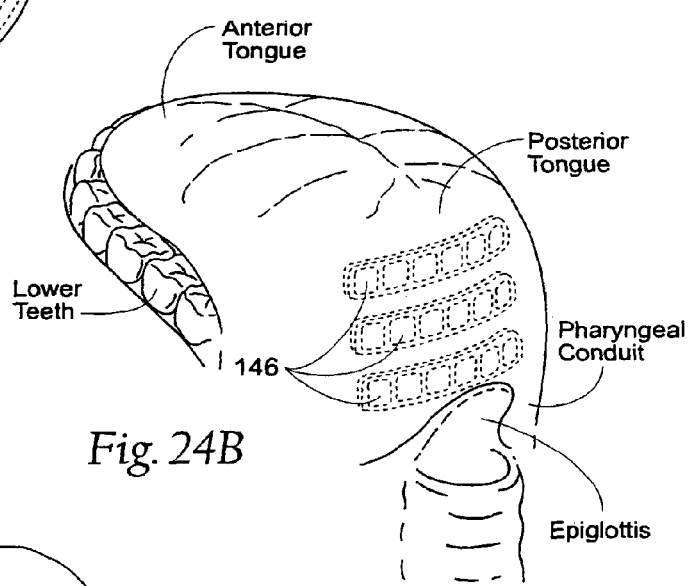

FIGS. 24A and 24B show the horizontal orientation of multiple sources of magnetism 146 in the tongue for use with the system 10 shown in FIG. 2.

FIGS. 25A, 25B, 25C, and 25D show the horizontal orientation of multiple sources of magnetism in the pharyngeal wall for use with the system 10 shown in FIG. 2.

Figure 26A:
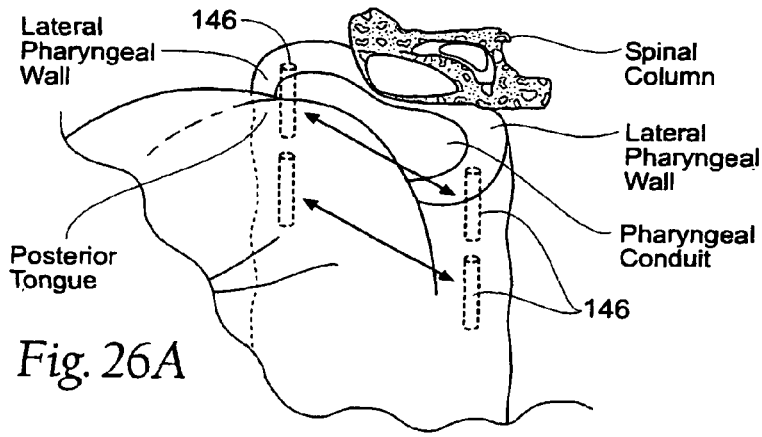
Figure 26B:
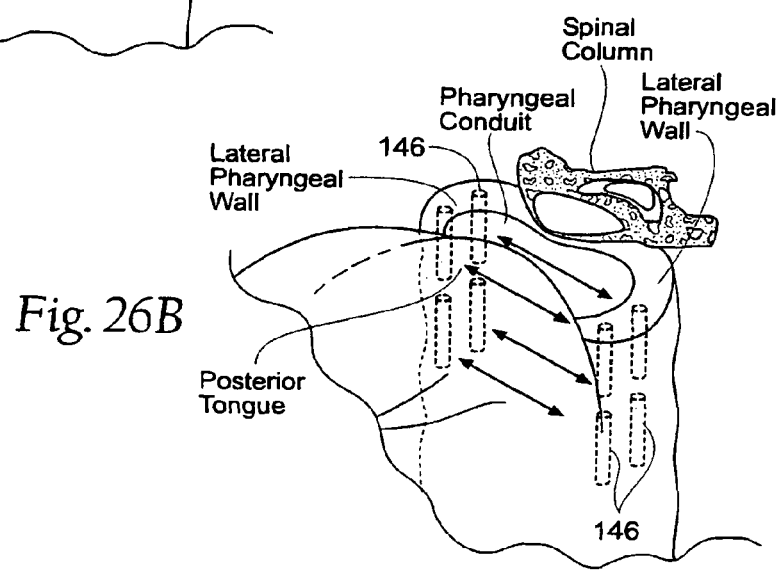
Figure 26C:
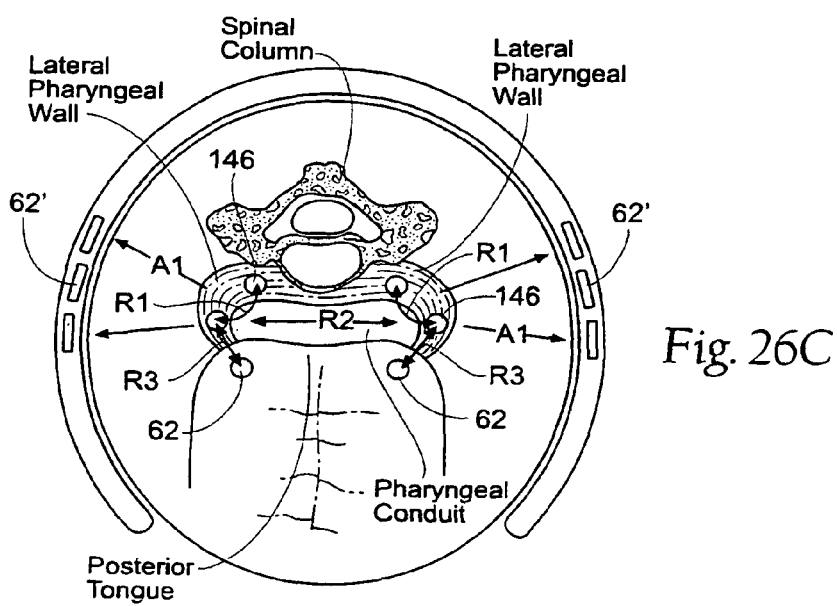

FIGS. 26A, 26B, 26C show the vertical orientation of multiple sources of magnetism in the pharyngeal wall for use with the system 10 shown in FIG. 2.

Figure 27A:
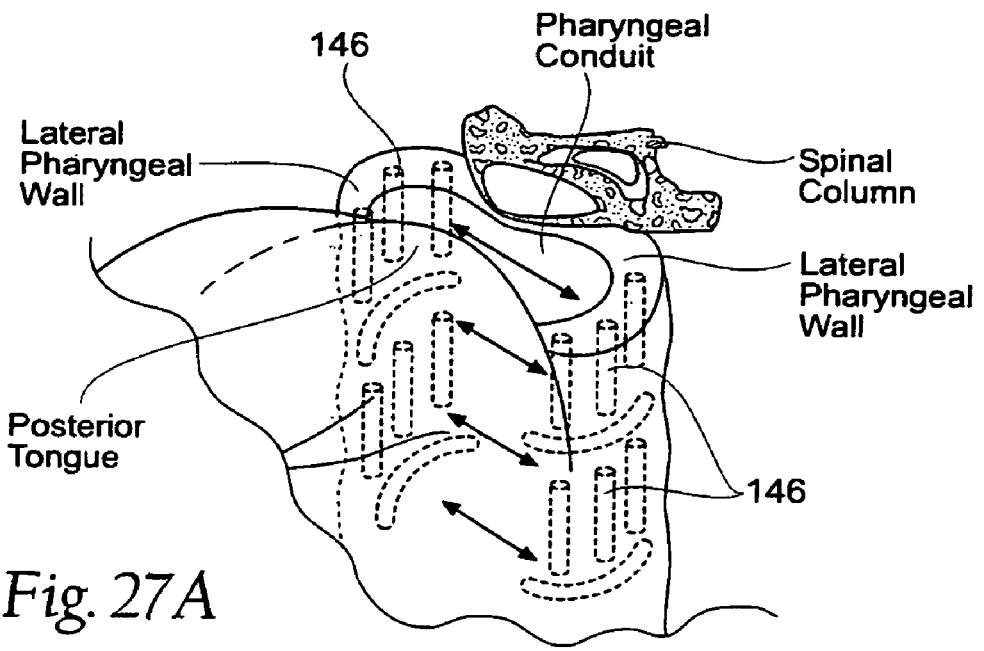
Figure 27B:
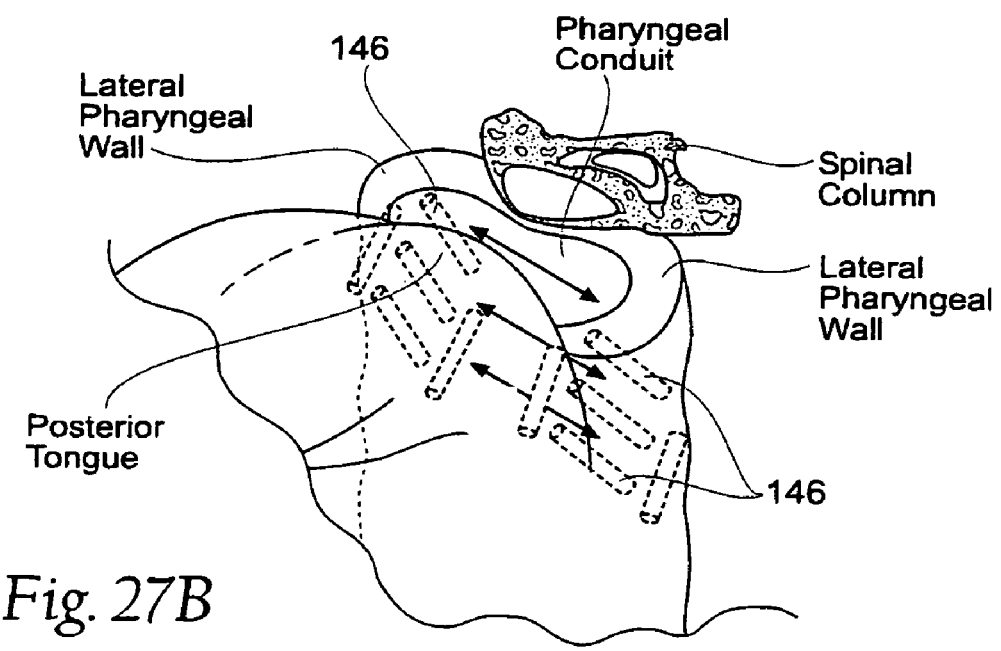

FIGS. 27A and 27B show, respectively, the horizontal and vertical orientation of multiple sources of magnetism in the pharyngeal wall for use with the system 10 shown in FIG. 2 and the angular orientation of multiple sources of magnetism in the pharyngeal wall for use with the system 10 shown in FIG. 2.

FIGS. 28A, 28B, 28C, 28D show a type of system 10 that includes ferromagnetic material or materials that are implanted in targeted pharyngeal structures in the pharyngeal conduit, which interact with source or sources of magnetic forces that are also implanted in targeted pharyngeal structures and individual anatomic components in the pharyngeal conduit, generating repelling forces to achieve the desired physiologic response.

Figure 29:
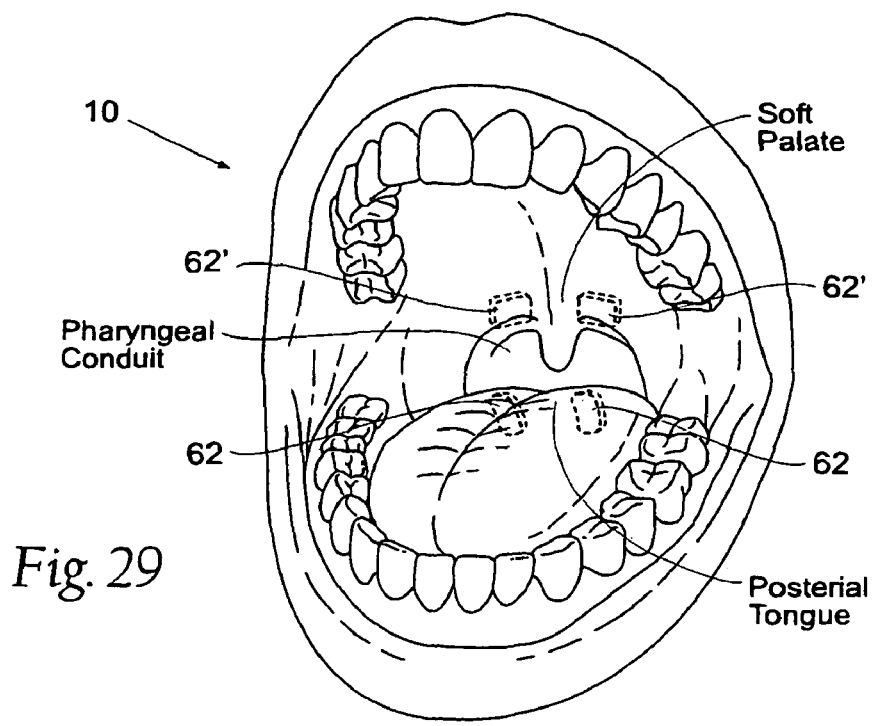

FIG. 29 shows a type of system 10 that includes ferromagnetic material or materials that are implanted in the tongue, which interact with source or sources of magnetic forces that are implanted in the soft palate, generating repelling forces to achieve the desired physiologic response.

Figure 30A:
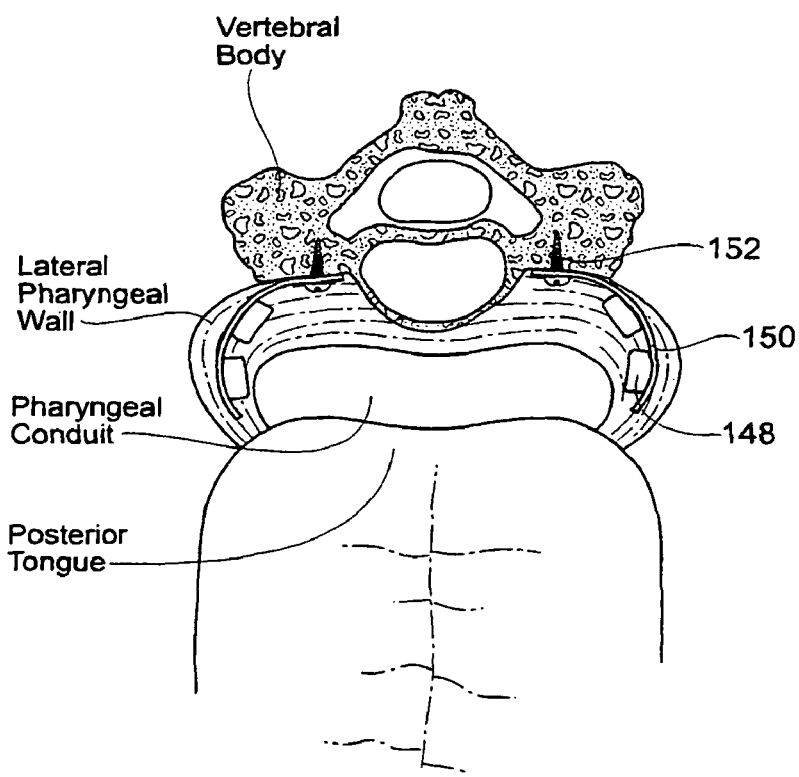
Figure 30B:
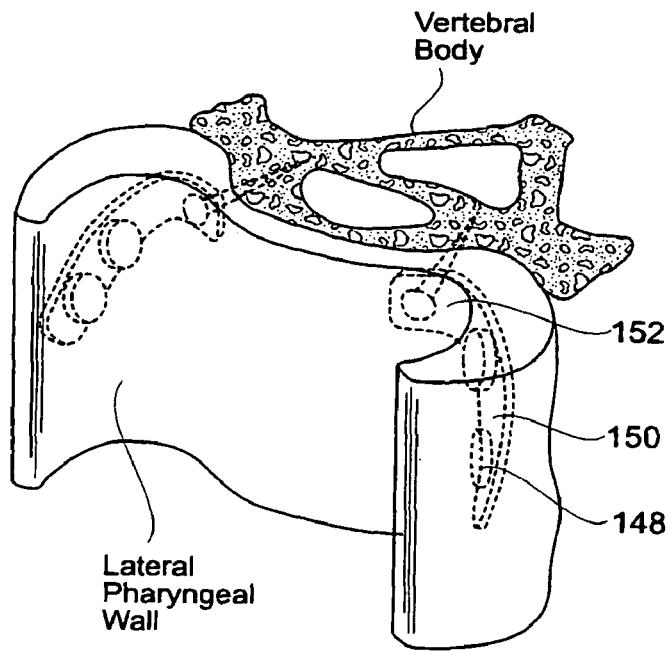
Figure 30C:
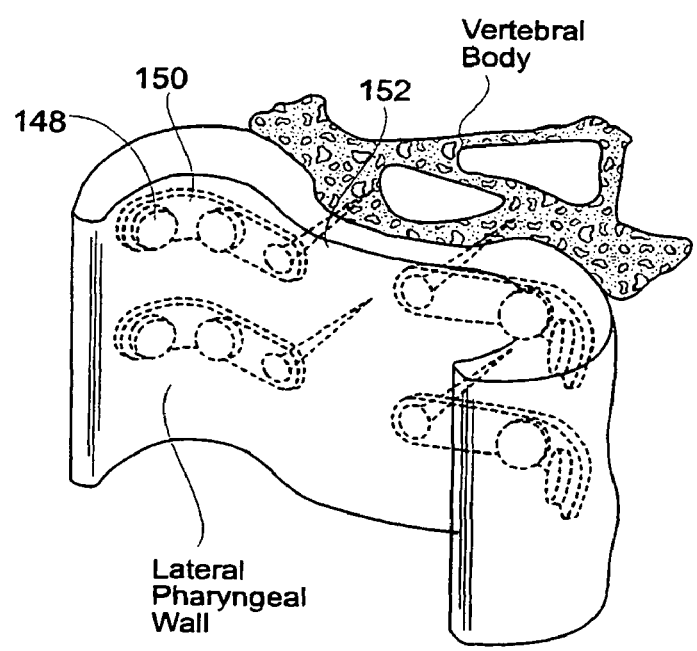

FIGS. 30A, 30B, and 30C show the implantation of a pharyngeal wall device within the pharyngeal conduit, with fixation to a vertebral body.

Figure 31:
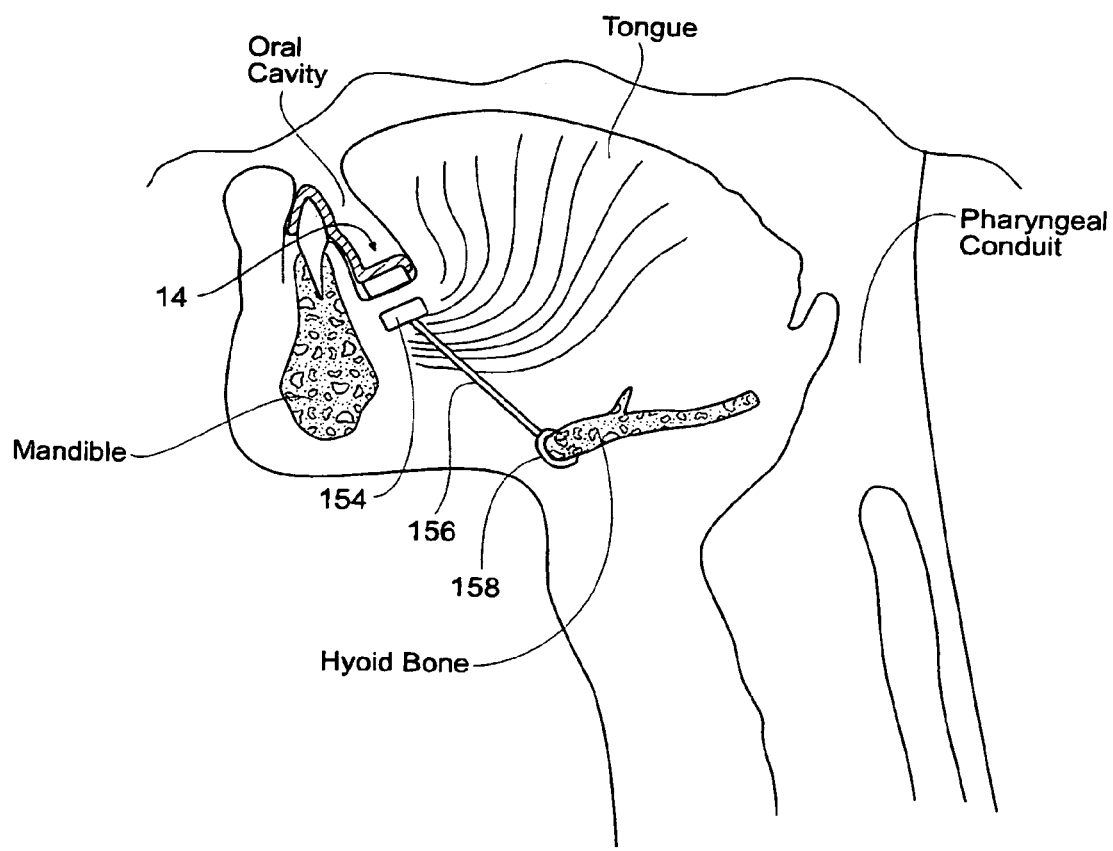

FIG. 31 shows the implantation of one or more permanent magnets of soft ferromagnetic materials outside the pharyngeal conduit, with fixation to the hyoid bone.

Figure 32A:
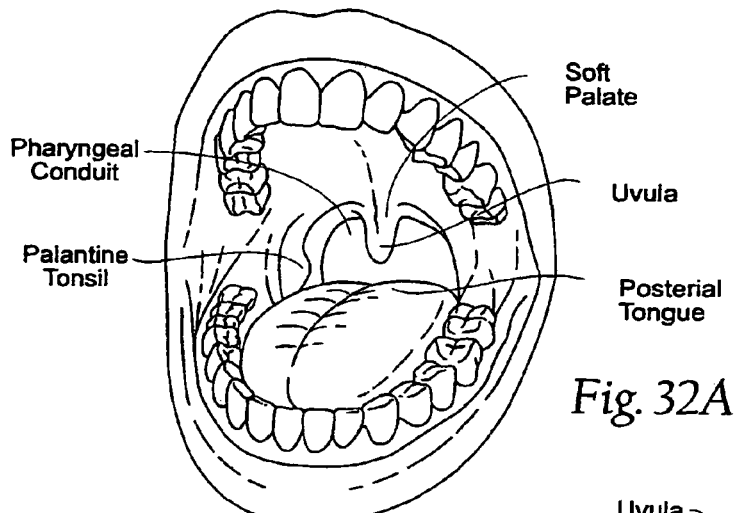
Figure 32B:
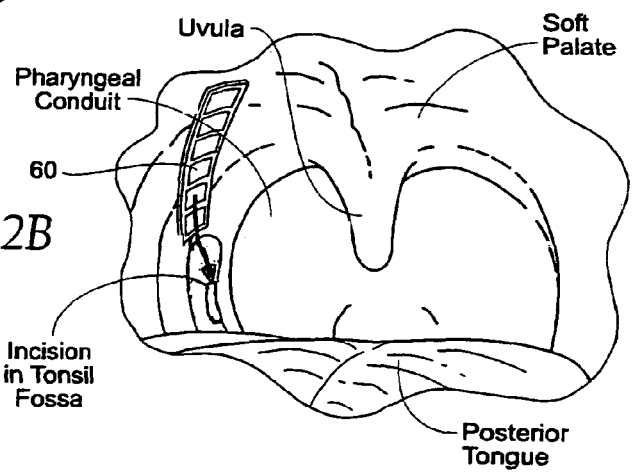
Figure 32C:
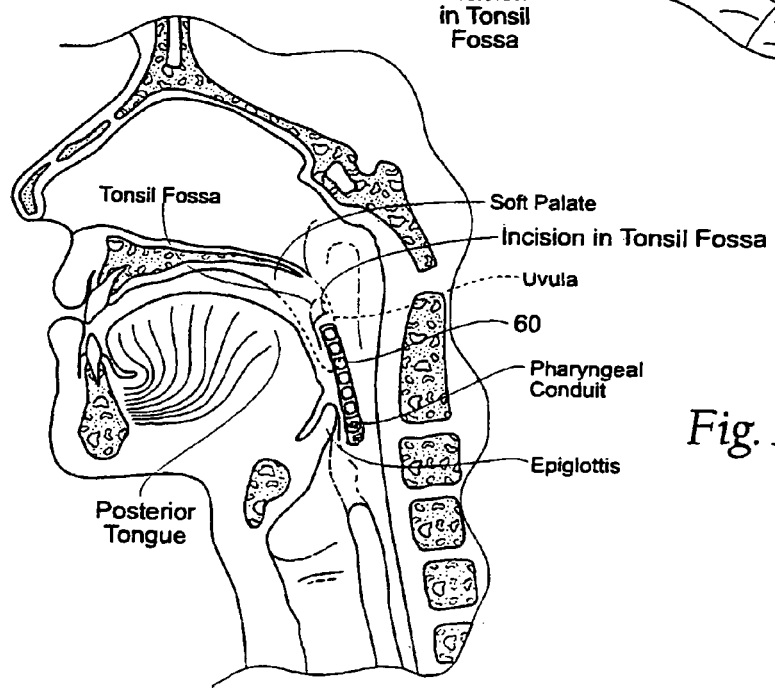

FIGS. 32A, 32B, and 32C show implantation of a pharyngeal wall device within the pharyngeal conduit through the fossa of the palatine tonsil.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Magnetic Force Systems

FIG. 2 shows in a diagrammatic way a magnetic force system 10. In use, the magnetic force system 10 resists the collapse of tissue in targeted pharyngeal structures and individual anatomic components within the pharyngeal conduit during sleep.

In its most basic form, the magnetic force system 10 comprises at least one ferromagnetic material 12 and at least one source 14 of magnetic force. The ferromagnetic material 12 is implanted in a targeted tissue region within the pharyngeal conduit. The source 14 of magnetic force interacts with the implanted ferromagnetic material 12, as shown by arrows in FIG. 2. The magnetic force creates a magnetic field within the targeted tissue region to achieve the desired physiologic response, which is to resist the collapse of tissue in targeted pharyngeal structures and individual anatomic components within the pharyngeal conduit during sleep.

Figure 1A:
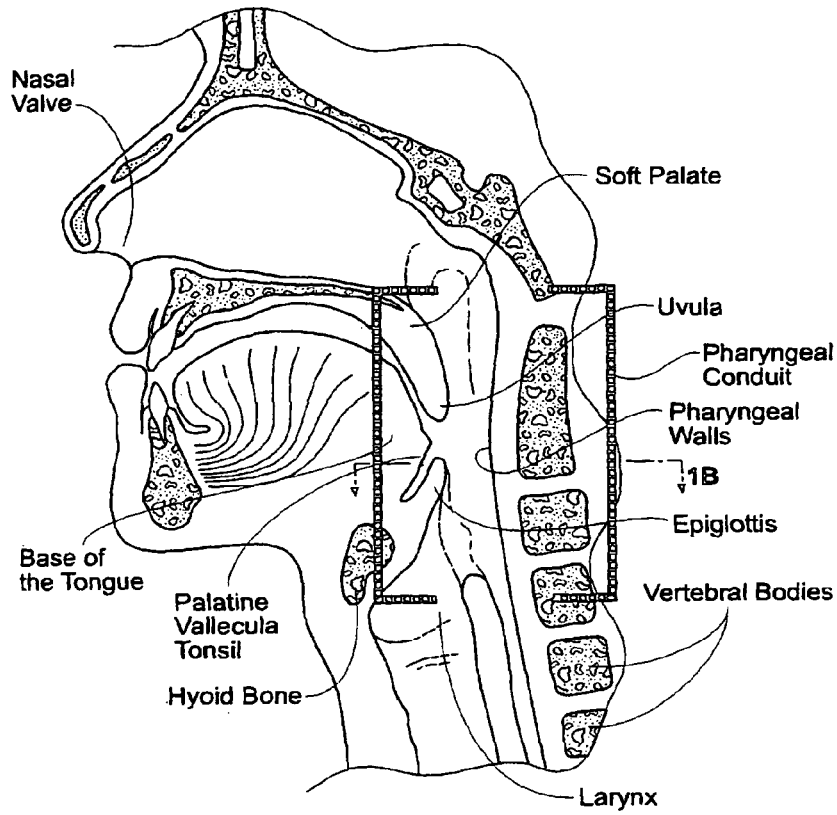
FIGS. 1A and 1B are anatomic views of the upper airway in a human, showing certain pharyngeal structures and individual anatomic components within the pharyngeal conduit, FIG. 1A comprising a lateral view
Figure 1B:
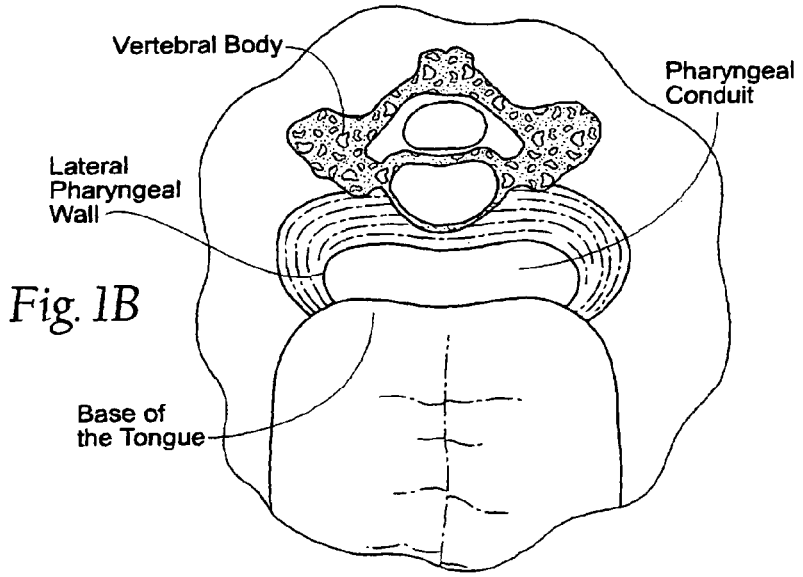

The targeted pharyngeal structures and individual anatomic components within this region can include the pharyngeal walls; the base of the tongue; the vallecula; the hyoid bone and its attachments; the soft palate with uvula; the palatine tonsils with associated pillar tissue; and the epiglottis. These anatomic regions are shown in FIGS. 1A and 1B. Representative examples of embodiments of magnetic force systems 10 in certain targeted pharyngeal structures and individual anatomic components within the pharyngeal conduit will be described in greater detail later.

A. The Implanted Ferromagnetic Material

The ferromagnetic material 12 is a material that has permeabilities ($\gamma$) greater than 1. A given ferromagnetic material can be "Hard" or "Soft."

A "Hard" ferromagnetic material is commonly referred to as a permanent magnet. A permanent magnet is characterized as showing resistance to external demagnetizing forces once being magnetized. A high external magnetic field is required in order to remove the residual magnetism of a permanent magnet. Stated differently, a permanent magnet has very high intrinsic coercivity, which is a measure of its resistance to demagnetization.

A permanent magnet will generate an external magnetic field, which can exert either an attracting force or a repelling force on a neighbor magnet(s). A permanent magnet possesses poles of opposite polarity. The poles are locations where magnetic attraction is realized. Relative to Earth's geographic poles, if the magnet is free to turn, one pole will point to the geographic north pole, and is thus called a North pole, and the opposite pole is likewise called a South pole of the magnet. The geographic north pole of the earth is its magnetic south pole, which attracts the north pole of permanent magnets. According to physical laws, poles of like polarity (North-North or South-South) repel each other with a magnetic force. On the other hand, poles of unlike polarity (North-South or South-North) attract each other with a magnetic force. The force of magnetic attraction or repulsion depends on the strength of the magnets and the distance between the poles. Thus, permanent magnets will repel each other if like poles face each other, and attract each other if opposite poles face each other.

Examples of known permanent magnet materials include alloys of Neodymium-Iron-Boron (NdFeB), alloys of luminum-Nickel-Cobalt (AlNiCo), and Samarium Cobalt (SmCo).

An electromagnet (current flowing through a coil of wire) can be substituted for a permanent magnet.

A "Soft" ferromagnetic material is a material that can be demagnetized very easily, once having been magnetized. In other words, a soft ferromagnetic material retains almost no residual magnetism after the magnetizing force is removed. Soft ferromagnetic materials have very high permeability and saturation magnetization, but very low intrinsic coercivity. Soft magnetic materials can be attracted by a permanent magnet or an electromagnet.

Examples of known soft ferromagnetic materials include Iron (Fe); Nickel (Ni); Permendur; MuMetal, low-carbon steels, Iron-Cobalt alloys (Fe—Co); silicon steels; and amorphous alloys.

B. The Source of Magnetic Force

The magnetic force source 14 comprises a permanent magnet. An electromagnet (current flowing through a coil of wire) can be substituted for the permanent magnet and serve as the magnetic force source.

The magnetic force source 14, like the ferromagnetic material 12, can be implanted in a targeted tissue region within the pharyngeal conduit. Illustrative examples of implanted sources 14 will be described later. Alternatively, as shown in phantom lines in FIG. 2, the magnetic force source 14 can be implanted or otherwise carried external to a pharyngeal structure region, e.g., in the oral cavity, neck, head, or mandible. Illustrative examples of external sources 14 will also be described later.

The magnetic field created by the magnetic force may be variously configured. For example, the magnetic field may be configured to attract the implanted ferromagnetic material 12. Conversely, the magnetic field may be configured to repel the implanted ferromagnetic material 12. The nature of the magnetic field depends upon the type of ferromagnet material 12 that is implanted, and the type of the magnetic force applied. These are, in turn, dictated by the type of physiologic response desired, given the anatomic orientation of the system 10. These aspects of the magnetic force system 10 will be discussed and illustrated in greater detail later.

II. Illustrative Ferromagnetic Material Designs Useable with the Magnetic Force System A. Permanent Magnets with Radial Magnetization As before stated, the implanted ferromagnetic material 12 and/or the source 14 of magnetic force can comprise a permanent magnet. The permanent magnet can be configured in various ways and take various shapes. e.g., cylindrical, square, rectangular, or other polygons.

Permanent magnets with radial magnetization may be desirably, because they direct magnetic flux in directions that extend radially from the center of the body of the magnet. Because of the radial magnetic flux directions, the permanent magnet presents the same magnet pole (north or south) about its entire outer surface.

Figure 3A:
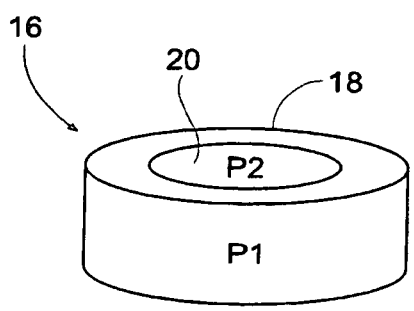
FIGS. 3A, 3B, and 3C are illustrative types of cylindrical permanent magnets having radial magnetization that can be used as an implanted ferromagnetic material and/or a source of magnetic force in the system 10 shown in FIG. 2.
Figure 3B:
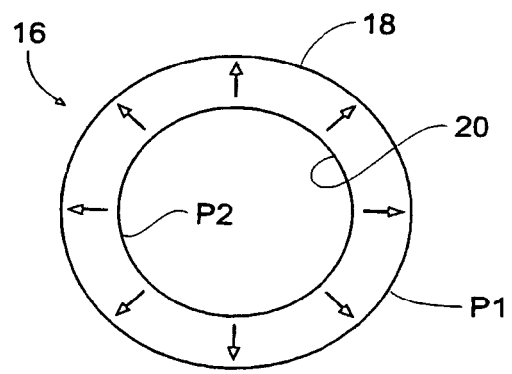
Figure 3C:
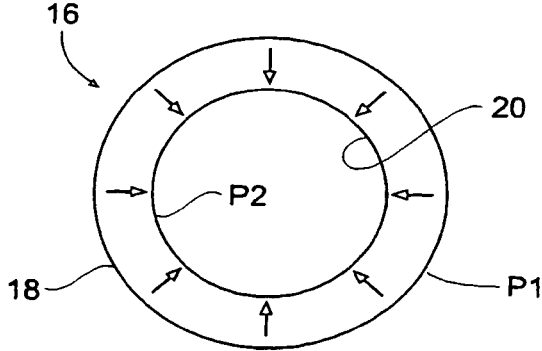

For example, FIG. 3A shows a cylindrical permanent magnet 16 having radial magnetization that can be used as an implanted ferromagnetic material 12 and/or a source 14 of magnetic force in the system 10 shown in FIG. 2. The cylindrical permanent magnet 16 has an outer diameter 18 and an inner diameter 20. Due to its radial magnetization, one magnetic pole P1 is on the outer diameter 18, and one magnetic pole is on the inner diameter 20. FIG. 3B is a cross section of the cylindrical permanent magnet 16 magnetized such that the north pole is on the outer diameter 18 and the south pole is on the inner diameter 20. FIG. 3C is a cross section of the cylindrical permanent magnet magnetized such that the south pole is on the outer diameter 18 and the north pole is on the inner diameter 20. In FIGS. 3B and 3C, arrows show the respective directions of magnetic moment or flux. The direction of magnetic moment or flux is also called the magnetization direction or magnetic orientation direction. In FIGS. 3B and 3C, the orientation can be seen to lie in radial paths from the center of the magnet body, hence the descriptive terminology "radial magnetization."

FIG. 4A shows a cylindrical permanent magnet assembly 22 having radial magnetization that can be used as an implanted ferromagnetic material 12 and/or a source 14 of magnetic force in the system 10 shown in FIG. 2. In FIG. 4A, the radial orientation is achieved by the assembly of radially magnetized arc segments 24. The assembly 22 of arc segments 24 collectively forms an outer diameter 26 and an inner diameter 28. In FIG. 4A, eight arc segments 24 form the assembly 22. It should be understood that a few or greater number of arc segments 24 can be used. As a general rule, however, the greater the number of arc segments 24 in a given assembly 22, the better the assembly 22 achieves the desired radial orientation. The limitation on the number or arc segments 24 is, of course, the size of the assembly 22. FIG. 4B is a cross section of the cylindrical permanent magnet assembly 22 with the eight arc segments 24 magnetized such that the north pole is on the outer diameter 26 and the south pole is on the inner diameter 28 of the assembly 22. FIG. 4C is a cross section of the cylindrical permanent magnet assembly 22 with the eight arc segments 24 magnetized such that the south pole is on the outer diameter 26 and the north pole is on the inner diameter 28 of the assembly 22. In FIGS. 4B and 4C, arrows show the respective directions of magnetic moment or flux, and the orientation can be seen to lie in radial paths from the center of the assembly.

Permanent magnets with radial-like magnetism can be created in other ways. For example, FIG. 5A shows two permanent ring magnets 30 and 32 magnetized along the axis of the respective body of each magnet. In this arrangement, one pole P1 is on one axial end of the magnet ring body 30/32, and the other pole P2 is on the opposite axial end of the magnet ring body 30/32. The two magnet ring bodies 30 and 32, each with axial magnetization, can be assembled together with like poles facing each other, to create an assembly 34.

FIG. 5B shows the assembly 34 of two magnet ring bodies 30 and 32, assembled together with like north poles facing each other. FIG. 5C is a cross section of the assembly 34 shown in FIG. 5B. As FIG. 5C shows, based upon finite element analysis, the assembly 34 possesses a radial-like orientation, with the north pole on the outer diameter 36 and the south pole on the inner diameter 38.

Figure 5D:
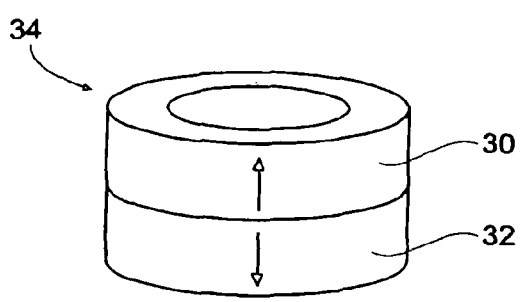
Figure 5E:
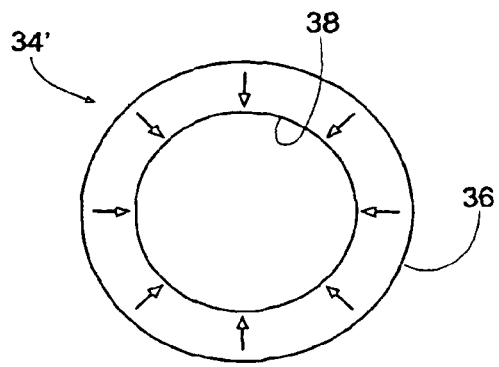

FIG. 5D shows the assembly 34' of two magnet ring bodies 30 and 34, assembled together with like south poles facing each other. FIG. 5E is a cross section of the assembly 34' shown in FIG. 5D. As FIG. 5E shows, based upon finite element analysis, the assembly 34' possesses a radial-like orientation, with the south pole on the outer diameter 36 and the north pole on the inner diameter 38. In FIGS. 5C and 5E, arrows show the respective directions of magnetic moment or flux, and the orientation can be seen to lie in radial paths from the center of the assembly.

Figure 5F:
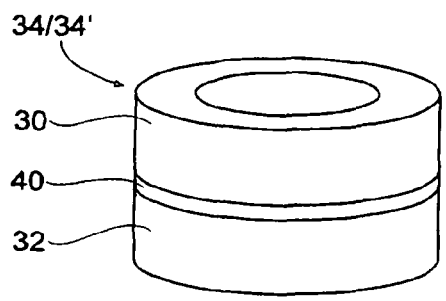

In the assembly 34 or 34' of either FIG. 5B or 5D, a spacer 40 can be introduced between the magnet ring bodies 30 and 32. FIG. 5F shows the presence of the spacer 40 between the two magnet ring bodies 30 and 32. The spacer 40 improves the repelling force between magnets of this type and neighboring magnet(s). The spacer 40 can comprise any soft ferromagnet material, such as iron, low-carbon steel, Fe—Co alloys, silicon steels, permendur, or amorphous alloys. The spacer 40 can also comprise non-magnetic materials or polymers, although the use of soft magnetic materials is preferred to maximize the enhancement of the repelling force.

Figure 6A:
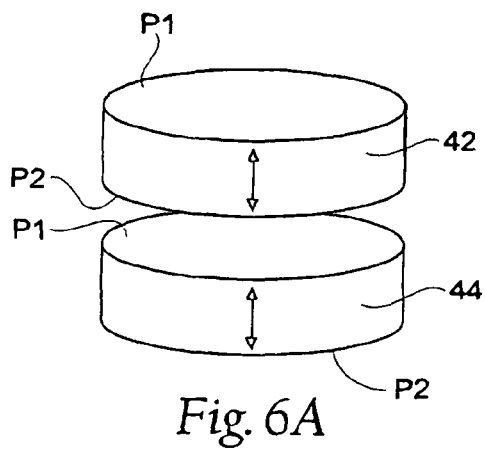
FIGS. 6A, 6B, 6C, 6D, and 6E, are illustrative types of permanent magnets comprising axially magnetized permanent disc magnets that, when assembled, have radial magnetization that can be used as an implanted ferromagnetic material and/or a source of magnetic force in the system 10 shown in FIG. 2.

As another example, FIG. 6A shows two permanent disc magnets 42 and 44 magnetized along the axis of the respective body of each magnet. In this arrangement, one pole P1 is on one axial end of the magnet disc body 42/44, and the other pole P2 is on the opposite axial end of the magnet disc body 42/44. The two magnet disc bodies 42 and 44, each with axial magnetism, can be assembled together with like poles facing each other, to create an assembly 46.

Figure 6B:
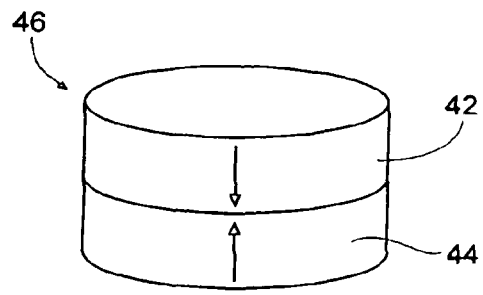
Figure 6C:
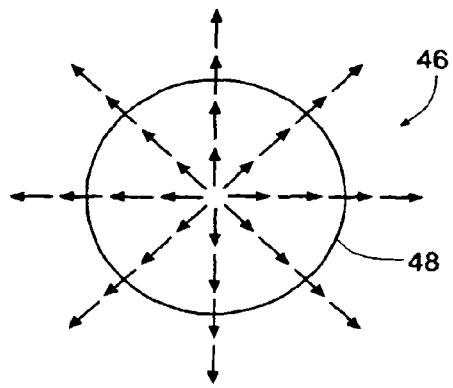

FIG. 6B shows the assembly 46 of two magnet ring bodies 42 and 44, assembled together with like north poles facing each other. FIG. 6C is a finite element analysis of the flux directions in a cross section of the assembly 46 shown in FIG. 6B. As FIG. 6C shows, the assembly 46 possesses a radial-like orientation, with the north pole on the outer diameter 48 of the assembly 46.

Figure 6D:
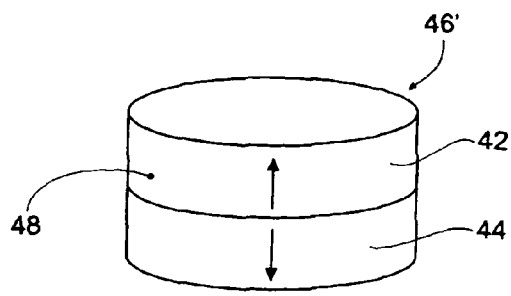

Conversely, FIG. 6D shows the assembly 46' of two magnet ring bodies 42 and 44, assembled together with like south poles facing each other. Finite element analysis, of the type shown in FIG. 6C, demonstrates the assembly 46' possesses a radial-like orientation opposite to that shown in FIG. 6C, with the south pole on the outer diameter 48.

Figure 6E:
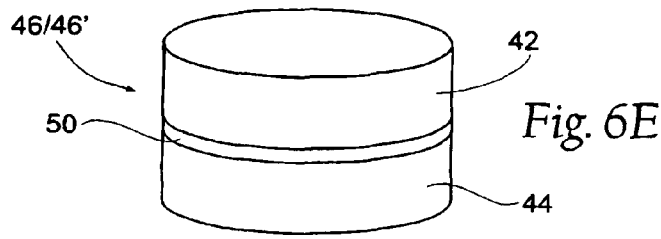

In the assembly 46 or 46' of either FIG. 6B or 6D, a spacer 50 can be introduced between the magnet disc bodies 42 and 44, as FIG. 6E shows. As before described, the spacer 50 improves the repelling force between magnets of this type and neighboring magnet(s). The spacer 50 can comprise any soft ferromagnet material or non-magnetic material, although the use of soft magnetic materials is preferred to maximize the enhancement of the repelling force.

B. Coils of Soft Ferromagnetic Material

As before stated, the implanted ferromagnetic material 12 can comprise a soft ferromagnetic material. The soft ferromagnetic 12 material can be configured in various ways.

Figure 7A:
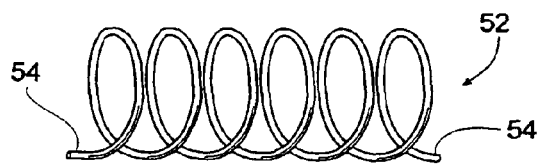
FIGS. 7A and 7B show a soft ferromagnetic material configured as a coil that is sized and configured to be used as an implanted ferromagnetic material in the system 10 shown in FIG. 2.

FIG. 7A shows, for example, a soft ferromagnetic material configured as a coil 52. The coil 52 is sized and configured to be suited for implantation in a targeted tissue region within the pharyngeal conduit.

The coil configuration lends flexibility to the magnet. This flexibility allows the implant to readily adopt to the anatomy and motion of tissue in which it is implanted. The flexibility also allows implantation of the coil without stiffening the tissue in which it is implanted. The coil 52 in a targeted tissue region within the pharyngeal conduit desirably is formed with atraumatic terminations 54.

Figure 7B:
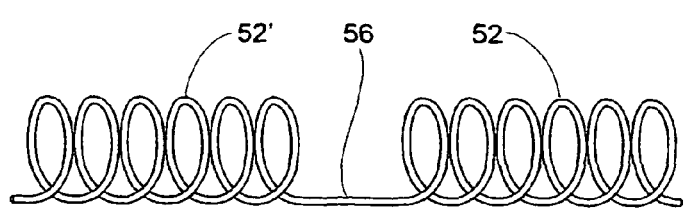

The coil 52 can be segmented for shorted lengths. The shorter lengths 52' could be coupled together by a polymer connecting material 56, as FIG. 7B shows. It should be appreciated that any type of discrete magnets (hard, or soft, or electromagnetic) can be coupled together in this fashion.

C. Use of a Protective Material to Prevent Interaction Between the System and Tissues/Fluids of the Body As FIG. 8 shows, the ferromagnetic material 12 and/or the source 14 of magnetic force of whatever form or configuration are desirably coated, plated, encapsulated, or deposited with a selected protective material 58, particularly if intended to be implanted. The protective material 58 is selected to provide a corrosion resistant and biocompatible interface, to prevent interaction between the ferromagnetic material 12 and/or the source 14 of magnetic force and tissues/fluids of the body. The protective material 58 is also desirably selected to form a durable tissue interface, to provide longevity to the system component, and thereby provide resistance to structural fatigue and/or failure. Selected to provide these desired physical and physiologic benefits, the protective material 58 and its application to the system component are also desirably selected to avoid imparting stiffness to the system component itself.

The protective material 58 can be selected among various types of materials known to provide the desired biocompatibility, resistance to corrosion, and durability. For example, the protective material 58 can comprise titanium material plated, deposited, or otherwise coated upon the ferromagnetic material 12 and/or the source 14 of magnetic force. As another example, the protective material 58 can comprise a parylene coating. As other examples, the protective material 58 can comprise a silicone polymer, a non-toxic epoxy, a medical grade polyurethane, or a U.V. curable medical acrylic co-polymer.

The protective material 58 may also incorporate anticoagulants and/or antibiotics, particularly if the system 10 component is intended for implantation.

III. Illustrative Ferromagnetic Implant Assemblies Useable with the Magnetic Force System

A. Discrete Magnets

The implanted ferromagnetic material and/or the source of magnetic force can each comprise a single or descrete source of magnetism having a given desired orientation. For example, a single permanent magnet, comprising a body of a ferromagnetic material, can comprise a single source of magnetism having a given orientation.

As another example, bonded permanent magnets may be used. Bonded magnets can be flexible or rigid, and consist of powdered NdFeB, Ferrite or SmCo permanent magnet materials bonded in a flexible or rigid substrate of e.g., rubber, nitrile, polyethylene, epoxy, polyvinyl chloride, or nylon. The forming of the bonded magnet can be achieved by extrusion, compression molding, injection molding, calendering, or printing. Bonded magnets enable unique flexible designs, and durable high tolerance shapes that are otherwise difficult to achieve. Bonded magnet designs can be magnetized in variety of modes such as multiple faces, radial homopolar, axial, and diametrical, and can be in anisotropic or isotropic forms.

Alternatively, the implanted ferromagnetic material 12 and/or the source of magnetic force can comprise an array of individual sources of magnetism, each sharing a common desired orientation. The array can comprise individual sources of magnetism arranged in a closely spaced apart relationship, without direct attachment among them.

The placement of individual or discrete magnets may, given the circumstances and physiology of the patient, provide the physician greater flexibility in selection of specific areas for treatment. For instance, a given patient may have more or thicker tissue in certain areas and the increased volume may be contributing to airway obstruction. The physician may choose to locate additional repelling energy at that spot. Additionally, it may be found that it is easier and less invasive to place small individual magnets or ferrous shapes than placing long strips in the anatomy.

It may be desirable to have uneven numbers of magnets in any two opposing anatomical features. For instance, a magnet on one side of an anatomic structure may be faced with two magnets on the opposite side of the anatomic structure. It may be desirable to oppose a single magnet with 3 or 4 opposing magnets. The use of uneven numbers of magnets in opposing anatomic features allows for more variation in implant alignment.

B. Injected Soft Ferromagnetic Alloys

A soft ferromagnetic material may be implanted by injection into tissue. For example, a magnetorheological (MR) fluid composed of a soft ferromagnetic material suspended in an injectable media may be placed into tissue to achieve the desired physiologic response. The MR fluid is by definition at different viscosity levels based upon magnetic field exposure and the exposing field strength.

The MR fluid can be created by mixing powder, small beads, or shavings of the alloy or ceramic (e.g., iron oxide or carbonyl iron) with a biocompatible media to create a uniform dispersion of the alloy. The biocompatible media may comprise an Elastin™ media, or may comprise an oil or low viscosity liquid that is biocompatible or is packaged within a biocompatible compartment to facilitate pharyngeal wall shaping, positioning, or improving the tone of the tissue. The media that the MR fluid is injected within may be a polyvinyl acetate (PVA) or foam that is appropriately sealed to provide biocompatibility.

Alternatively, a powder, small beads, or shavings of soft ferromagnetic material alloy can be mixed with the dry component of two part polymethyl methacrylate (PMMA) cement. The liquid component would be added to polymerize the combination of dry monomer and soft ferromagnetic material alloy, to create an injectable acrylic for the use in the system 10. Once the suspension sets in situ it would have the intended anatomical shape and position to achieve the desired physiologic response. Additionally, the magnetic PMMA may be injected into implanted compartments to facilitate shaping and biocompatibility.

C. Flexible Magnetic Arrays

A flexible or compliant array of magnets can also comprise individual sources of magnetism carried as a unit on a support carrier, or otherwise directly linked together (for example, as magnets in FIG. 7B are joined by string or polymer material).

FIGS. 9A and 9B show flexible arrays 60 of ferromagnetic materials 62, which can comprise "hard" and/or "soft" magnets. The hard magnets can be magnetized through the thickness in a variety of modes, such as multipole faces, radial homopolar, axial, or diametrical. In FIGS. 9A and 9B, the ferromagnetic materials 62 comprise permanent magnets. In FIGS. 9A and 9B, the north pole is oriented in the direction shown by the arrows (i.e., the north pole is on top in FIG. 9A, and the south pole is on top in FIG. 9B). Like permanent magnets (having the same magnetic orientation) are assembled on a flexible polymer matrix 64. Further, the arrays 60 can be used in pairs or other combinations to provide either repelling or attracting forces in targeted pharyngeal structures and individual anatomic components within the pharyngeal conduit. FIG. 9C shows two arrays 60(1) and 60(2) arranged with like north poles facing each other A repelling force exists between the two arrays 60(1) and 60(2). In the context of the system 10 shown in FIG. 2, a first matrix 60(1) can be implanted, e.g., in a targeted tissue region to comprise a ferromagnetic material 12 of the system 10, and a second matrix 60(2) can be located, e.g., either by implantation within the pharyngeal conduit or by implantation or external placement outside the pharyngeal conduit, to comprise a source 14 of magnetic force of the system 10. As will be demonstrated in greater detail later, when magnetic arrays 60(1) and 60(2) are oriented in a desired relationship with respect to targeted pharyngeal structures and individual anatomic components within the pharyngeal conduit, the repelling force existing between the arrays 60(1) and 60(2) can be used to keep tissue from collapsing.

It should be appreciated that two arrays 60(1) and 60(2) arranged with south poles facing each other, when suitably placed in an adjacent facing relationship with respect to the pharyngeal conduit, will lead to the existence of repelling forces, and the same desired physiologic response.

FIG. 9D shows a first array 60(1) of the north pole orientation placed in an adjacent facing relationship with a second array 60(2) of the south pole orientation. An attracting force exists between the two arrays 60(1) and 60(2). In the context of the system 10 shown in FIG. 2, a first matrix 60(1) can be implanted, e.g., in a targeted tissue region to comprise a ferromagnetic material 12 of the system 10, and a second array 60(2) can be located, e.g., either by implantation in the pharyngeal conduit or by implantation or placement external to the pharyngeal conduit, to comprise a source 14 of magnetic force of the system 10. As will be demonstrated in greater detail later, when the arrays 60(1) and 60(2) are oriented in a desired relationship with respect to targeted pharyngeal structures and individual anatomic components within the pharyngeal conduit, the attracting force existing between the arrays 60(1) and 60(2) can be used to keep tissue from collapsing.

As FIG. 9E shows, machined, laser cut, chemically etched, or EDM manufactured soft ferromagnetic materials 66 (e.g., Hiperco 50A, HYMU-80, 99.95% Iron, or 410 Stainless Steel) can also be encased, packaged, or otherwise arranged on a flexible matrix 64, to form a magnetic array 60. In the context of the system 10 shown in FIG. 2, the array 60 can be implanted, e.g., in a targeted tissue region to comprise a ferromagnetic material 12 of the system 10. In this arrangement, the source 14 of magnetic force (which can comprise, e.g., a second array with permanent magnets, or a single permanent magnet, or an electromagnet) can be located, e.g., either by implantation in the pharyngeal conduit or by implantation or placement external of the pharyngeal conduit, to create an attracting force to keep implanted tissue from collapsing.

The matrix 64 is desirably made from a material that imparts biocompatibility, durability, and flexibility to the array. The matrix 64 may be made, e.g., of a semi-rigid polymeric material such as polycarbonate, silicone rubber, polyurethane, etc. The flexibility imparts improved comfort, tolerance, and bio-acceptance to the implant for the patient. The flexibility also allows the matrix 64 to conform to the anatomical feature into which the matrix 64 is implanted. As a result of the flexibility, the array 60 does not achieve the desired physiologic response (i.e., resisting tissue collapse) by indiscriminate stiffening of tissue in the pharyngeal conduit (which is not desirable), but instead achieves the desired physiologic response because of the controlled effect of the magnetic field, by pushing or pulling on tissue, which does not impart stiffness to the tissue in the pharyngeal conduit.

Flexible magnetic arrays 60 can be realized in various physical forms. FIG. 10A shows one illustrative embodiment of a magnetic strip array. In this embodiment, the individual magnets 62 or soft ferromagnetic materials 66 are encapsulated within a carrier strip material 68. The magnets 62 or soft ferromagnetic materials 66 are arranged in a spaced apart pattern within the carrier strip material 68. The carrier strip material 68 encloses the magnets 62 or soft ferromagnetic materials 66, thereby also providing the functional benefits of the protective material 58 discussed above. The spacing between the magnets 62 or soft ferromagnetic materials 66 within carrier strip material 68 provides the requisite flexibility desired.

The magnetic strip array 60 may have a straight edge as shown in FIG. 10A, or may be irregular or convoluted, as shown in FIG. 10B, to enhance anchoring within the tissue. The carrier strip material 68 may also be perforated or roughened for the same purpose. Further details of the benefits and desirability of tissue in-growth will be discussed later.

Flexible magnetic arrays 60 can also be created using bonded magnets, as already described.

FIG. 11 shows another embodiment of a magnetic strip array 60. This array 60 affixes magnets 62 or soft ferromagnetic materials 66 to a flexible polymeric strip 70. Areas 72 are formed in the strip that comprise "living hinges" between the magnets 62 or soft ferromagnetic materials 66. The living hinges 72 impart enhanced flexibility to the array 60. The living hinges 72 may be aligned with either axis of the array 60. As an alternate to the formed hinges 72, the flexing area may be convoluted as shown in reference numeral 74 in FIG. 11. Such convolutions 74, which may also be thinner than the rest of the carrier strip 70, may be used to provide controlled flexibility.

FIG. 12 shows another embodiment of a magnetic strip array 60. In this embodiment, "blister strips" 76 are vacuum or pressure formed of a bio-inert film, producing thin wall strips with pockets 78. These pockets 78 are sized and configured to receive the permanent magnets 62 or soft ferromagnetic materials 66. A bonding face 80 is provided on each half of the blister strip 76, providing a surface for adhesive or heat sealing of the opposing blister strips 76. When sealed into the formed film "blister package", the magnets 62 or soft ferromagnetic materials 66 will be protected from body fluids and are held in the desired orientation to one another. A narrow neck 82 provides a hinge, allowing the magnetic strip to flex as described in the previous embodiments. After sealing the opposing blister halves, the blister strip package 76 can be coated with appropriate materials to encourage in-growth and tissue anchoring, as will be described later.

It is believed that the use of flexible arrays of multiple magnets 62 or soft ferromagnetic materials 66 arranged on a flexible matrix 64—instead of using a single, larger magnet— is desirable. This is because magnets 62 or soft ferromagnetic materials 66 arranged in an array 60 on a flexible matrix 64 will provide conformability, tolerance, and comfort for the patient, and will not stiffen tissue. The use of a flexible matrix 64 holding an array 60 of individual, smaller magnets 62 or ferromagnetic materials 66 will also result a series of smaller, overlapping magnetic moment or flux fields. This is believed desirable over the use of single, larger magnets, which may result in a larger, monolithic magnetic flux field, without overlapping lines of flux.

The size of the flexible magnetic array 60, and the size of individual magnets 62 or soft ferromagnetic materials 66 in the array 60, are selected with the ease and bio-comfort of implantation in mind, while at the same time providing sufficient magnetic force to resist tissue collapse, taking into account the anatomy of the region of implantation and orientation of other components of the system 10. As one example, a size of 12 mm wide, 40 mm in height and 3 to 3.5 mm in thickness may be provided, while it is apparent that either larger or smaller implants will also achieve the desired physiologic response. Furthermore, the individual magnets 62 or soft ferromagnetic materials 66 can have various geometries—rectangular, cylindrical, spherical, oval, etc.—as long as the desired physiologic response is achieved.

Flexible magnetic arrays 60 are well suited for implantation in targeted pharyngeal structures and other anatomic components within the pharyngeal conduit, serving either as a ferromagnetic material 12 or a source 14 of magnetic force, or both. A flexible magnetic array 60 can implanted alone, or in combination with other ferromagnetic materials, or in series with other flexible magnetic arrays 60, or in parallel with other flexible magnetic arrays 60, or in one or more pairs of opposing magnetic strip arrays 60, and in either a horizontal or vertical anatomic orientation, and/or in a linear or curvilinear pattern within the pharyngeal conduit. For example (see FIG. 24), flexible magnetic arrays 60 carrying permanent magnets are well suited for implantation in the posterior of the tongue, with an array desirably positioned both laterally left and right of the centerline of the tongue. In this arrangement, other flexible arrays 60 of permanent magnets having the same magnetic orientation might then be implanted in tissue in the lateral pharyngeal wall directly opposite and posterior to the position of the tongue implants. The repelling force between the tongue implants and the implants in the lateral pharyngeal wall will resist collapse of the airway as the tissue relaxes and comes into proximity, particularly during Phase IV of the respiratory cycle. Several other arrangements are possible, as will be described in greater detail later.

In the context of the system 10 just described, the distance between repelling flexible magnetic arrays on the tongue and lateral pharyngeal wall should provide sufficient repelling force between the opposed arrays to prevent closure of an airway during sleep, but should not be so strong that it is difficult to swallow. The amount of force to accomplish this is believed to be greater than about 4 grams/cm$^2$.

In the flexible magnetic arrays 60 described, the polymer matrix 64 carrying the magnets 62 or soft ferromagnetic materials 64 has been configured as an elongated strip. It should be recognized that the arrays 60 need not necessarily take the form of elongated strips. The arrays 60 can take the form of circular, or rectangular, or square layouts. Virtually any configuration can be adopted to fit the anatomic requirements of the targeted implantation site and the overall desired physiologic response. Furthermore, the matrix 64 may carry more than a single row of magnets 62 or soft ferromagnetic materials 64. Multiple rows maybe carried on a given matrix 64.

D. Tethered Magnets

In some cases, the implantation of individual permanent magnets 62 or soft ferromagnetic materials 66 may be indicated for providing the desired physiologic response. When individual permanent magnets or soft ferromagnetic materials are implanted in tissue, it may be desirable to tether the magnet 62 or soft ferromagnetic material 66 to a holding or anchoring structure 84 that provides resistance against movement of the implant within tissue. This is particular relevant when the implantation region presents a relatively large, soft tissue mass, such as in the tongue. The tethering of the magnet(s) permits placement of the magnet(s) in closer proximity to the source 14 of magnetic force.

By way of example, FIG. 13A shows a permanent magnet 62 or soft ferromagnetic material 66 tethered by a band 86 to a holding or anchoring structure 84. The band 86 may comprise a non-resorbable suture material, other woven biocompatible lacing or fabric, a non woven polymer strip such as nylon or acetal or a biocompatible metallic material such as nickel titanium alloy (Nitinol®). While such materials are non-elastic, the band 86 may also be made of an elastic material. Such elasticity could provide compliance and increased comfort for the patient. For instance, when swallowing, the tongue moves in an anterior direction and elasticity may prevent arousal from sleep and further may avoid migration of the magnet 62 or soft ferromagnetic material 66.

The holding structure 84 is wider than the band 86, thereby providing resistance for the implanted magnet 62 or soft ferromagnetic material 66 against being pulled through or out of the implanted tissue region (which is shown in phantom lines in FIG. 13A).

The material of the holding structure 84 can be any biocompatible flexible metal or polymeric compound that will resist deterioration, while exhibiting sufficient flexibility to prevent discomfort or affecting speech or swallowing.

As shown in FIG. 13A, the holding structure 84 may include perforations 88. The perforations 88 impart greater flexibility to the holding structure 84. The perforations 88 also accommodate tissue in-growth, further securing the location of the implant and preventing migration.

As shown in FIG. 13B, multiple holding structures 84 may be attached to the magnet 62 or soft ferromagnetic material 66, to distribute the force over a greater area. FIG. 22C also illustrates the use of an implant (in the tongue) having multiple holding structures for the same purpose.

D. Fixation of Magnetic Implants

1. Use of Mechanical Fixation Materials

The position of implanted ferromagnetic materials 12 and sources 14 of magnetic force (when implanted) can be fixed against migration in a targeted tissue region within the pharyngeal conduit using conventional mechanical fixation materials and techniques known in the surgical arts, e.g., non-resorbable sutures, screws or staples. For example, the arrays of magnets 62 or soft ferromagnetic materials 66 shown in FIGS. 10, 11, and 12 can include preformed apertures 90 to accommodate the fixation material, i.e., sutures, screws or staples. In the embodiment shown in FIG. 13, the holding structures can include preformed apertures 90 for the same purpose.

The tissue to which a given magnetic implant is fixed can include soft tissue in the pharyngeal walls, the base of the tongue; the vallecula; the soft palate with uvula; the palatine tonsils with associated pillar tissue, and the epiglottis. The tissue can also include bone, e.g., the vertebral body or hyoid bone and its attachments, as will be described later.

2. Use of an Implantation Sleeve

As shown FIG. 14A, a single magnet 62 or soft ferromagnetic material 66, or an array 60 of magnets 62 or soft ferromagnetic materials 66 can be inserted during implantation into an implanted sleeve 92. The sleeve 92 would be placed, e.g., within an incision, in the targeted tissue region. The surgeon may anchor the sleeve 92 in place by suturing, stapling, or screwing. Following insertion and anchoring of the sleeve 92, the magnets 62/66 or magnetic array 60 would be placed into the sleeve 92, as indicated by the arrow in FIG. 14A. The top of the sleeve 92 and the opening of the incision would be closed by suturing or other accepted closure means such as stapling, etc.

Use of a sleeve 92 to receive the magnetic implant allows the surgeon to more readily change or titrate the type, strength or number of magnetic components implanted in the targeted tissue region. To make such a change, an incision would be made at the opening end of the sleeve 92 and the magnet or magnetic array would be slid out of the sleeve, then replaced by a different strength or type of magnet, if such a change was deemed desirable. This would be a simpler, faster and less morbid procedure than having to cut tissue surrounding the implant to remove an existing implanted array.

Use of a sleeve 92 also allows tissue in-growth to the sleeve 92 to take place at the implantation site before the ferromagnetic material is installed.

The sleeve 92 is made of a material having the characteristics of the protective material 58, already described. In addition, the sleeve material also desirably accommodates or encourages tissue in-growth, as will be described shortly.

In FIG. 14B, the sleeve 92 may include an integrated anchoring device that imparts increased stability and anchoring of the sleeve 92 within the tissue. In this embodiment, the sleeve 92 includes wings or barbs 94 that can be deployed into surrounding tissue after implantation of the sleeve 92. The deployment of the wings 94 at the appropriate time can be achieved in various ways. For example, each wing 94 may include a hinged support arm 96. As an actuator tool T is inserted into the sleeve 92 (shown in phantom lines in FIG. 14B, the actuator tool T contacts the support arms 96 in succession. When contacted by the tool T, each support arm 96 in succession swings, pivoting about the hinge point, deploying the wing 94 into tissue. The tip of the wing 94 may be configured to cause blunt penetration of the tissue or, may be sharp if reduced penetrating forces are desired. Once all wings 94 are deployed, the actuator tool T is withdrawn, and the magnet 62/66 or magnetic array 60 is inserted into the sleeve 92. Alternatively, the insertion of the magnet 62/66 or magnetic array 60 may be used to deploy the wings 94, in which case a separate actuator tool T would not be required.

It should be appreciated that wings 94 may be incorporated directly onto a magnetic array 60, with use of a sleeve 92.

The wings 94 provide increased stabilization and resistance to the sleeve 92 against rotation and migration within tissue. This may reduce the need for enhanced tissue in-growth and make removal of any implanted device a simpler and safer procedure. In the event there is a reason to remove the sleeve 92, the wings 94 are configured to withdraw from the tissue in response to withdrawal of the sleeve 92 from the implantation site.

3. Magnet-Staple Assembly

FIG. 15A shows a magnet-staple assembly 98 comprising a permanent magnet 62 or soft ferromagetic material 66 that includes an attached or integrated stapling flange 100. The integrated stapling flange 100 makes possible the implantation of the magnet-staple assembly 98 within the mucosa of tissue within the pharyngeal conduit, as close to the tissue surface as possible. In this way, the magnet-staple assembly 98 follows the compliance of the soft tissue in the targeted implant area, particularly in its most relaxed state, when tissue collapse can occur during sleep.

The magnet-staple assembly 98 can be stapled within the interior of a tissue flap or incision, to minimize direct exposure of the magnetic element to the pharyngeal conduit. In this arrangement, only the staple flange 100 would be exposed to the interior of the pharyngeal conduit at its bends, which would project outward from within the tissue flap or incision. In this situation, the incision can be sealed with a bioadhesive or sealant.

Alternatively, the magnet-staple assembly 98 could be stapled directly to targeted pharyngeal structures and anatomic components within the pharyngeal conduit, leaving most of the magnet-staple assembly 98 exposed. In this situation, tissue healing can be encouraged by coating the magnet-staple assembly 98, e.g., with a hydrogel doped with or treated with a wound-healing drug.

A single magnet-staple assembly 98 can be implanted in a targeted tissue region. Alternatively, magnet-staple assemblies 98 could be implanted in multiple locations in targeted pharyngeal structures and anatomic components within the pharyngeal conduit in horizontal and/or vertical arrangements (see FIG. 15B) selected to repel or attract neighboring magnets, as required to achieve the desired physiologic response.

The stapling flange 100 can be attached to the permanent magnet 62 or soft ferromagnetic material 66 in various ways. For example, electro-forming, bonding, or comparable means could be used to integrally attach the stapling flange 100 to the permanent magnet 62 or soft ferromagnetic material 66. Alternatively, as shown in FIG. 15C, the staple component 102 could be separately formed by metal etching or laser cutting. In this arrangement, the staple component 102 includes tabs 104 to receive and mechanically grasp and hold the magnet 62 or soft ferromagnetic material 66, thereby forming the composite magnet-staple assembly 98.

The staple portion 102 of the magnet-staple assembly can be made of stainless steel or nickel titanium Nitinol™ (NiTi) material. When electroformed, the material may be any electro-deposited metal material selected for its ductility, e.g., gold or platinum.

4. Fixation to Bone within the Pharyngeal Conduit (Vertebral Body)

In some cases, implantation of one or more permanent magnets or soft ferromagnetic material in the pharyngeal conduit, with fixation to bone, may be indicated. FIGS. 30A, 30B, and 30C show magnets 148 attached to flexible, non-magnetic flexible arms 150 that are implanted in one or more lateral pharyngeal walls and that are, further, fixed to a vertebral body with bone screws 152. Fixation to bone stabilizes the position of implanted magnets. The arms 150 may be oriented horizontally in a single row or in a vertically stacked relationship along the pharyngeal conduit (as shown in FIG. 30C), in an angular path within a lateral pharyngeal wall (as shown in FIG. 30B). Depending upon orientation, the arms 150 can be shaped to conform to the morphology of the tissue.

5. Fixation to Bone Outside the Pharyngeal Conduit (Hyoid Bone)

Implantation of one or more permanent magnets or soft ferromagnetic material outside the pharyngeal conduit, with fixation to bone, may also be indicated. For example, the hyoid bone has cartilage and muscles attached, and movement of the hyoid bone can affect the pharynx and tissues surrounding the pharyngeal conduit. In some patients, preventing anterior and inferior movement of the hyoid bone can assist in keeping the pharyngeal conduit open.

FIG. 31 shows a magnet 154 (which can comprise a soft ferromagnetic material or a permanent magnet) tethered to the body of hyoid bone by a cord or band 156. The cord or band is attached by a crimp ring 158 to the body of the hyoid bone (531). The band 156 may comprise a non-resorbable suture material, other woven biocompatible lacing or fabric, a non woven polymer strip such as nylon or acetal or a biocompatible metallic material such as nickel titanium alloy (Nitinol®).

The cord or band 156 allows the magnet 154 to be placed in proximity to the mandible symphis. The cord or band 156 also transmit forces acting upon the magnet 154 to the hyoid bone.

In use, the implanted magnet 154 can interact with a source 14 of magnetic force, positioned, e.g., in the oral cavity (an oral appliance suited for this purpose will be described in greater detail later). The magnetic interaction with the source 14 can, e.g., attract the implanted magnet 154, exerting a force (via the band 156) in an upward/forward direction upon the hyoid bone. The magnetic attraction keeps an angular upward and forward force on the hyoid bone, preventing droop downward and backward and thereby assisting in maintaining the pharyngeal conduit open.

6. Tissue In-Growth Surfaces

In addition to any of the just-described tissue fixation methodologies (see FIG. 16), the magnetic implant (generally designated MI in FIG. 16) can include a tissue in-growth surface 106. The surface 106 provides an environment that encourages the in-growth of neighboring tissue on the magnetic implant MI. As in-growth occurs, the implanted magnetic implant MI will become securely anchored, resisting migration or extrusion from the tissue. The tissue in-growth surface 106 thus enhanced tissue adhesion and stabilization, and thereby further stabilizes and fixes the position of the magnetic implant MI in the targeted implantation site.

The tissue in-growth surface 106 can be formed in various ways. For example, the surface 106 can comprise an open cellular or fibrous structure, biologically inert in nature and known to support in-growth by body tissue. One material that exhibits this characteristic is expanded PTFE (polytetrafluoroethylene or Teflon®—DuPont). This material may be prepared by radiation bombardment to cause the structure of the material to become fractured and fibrous in nature. The resulting material is open and porous, providing fissures into which fluids may enter and to which body tissue can attach and grow. Other such inert polymers and even metals (such as nickel titanium—Nitinol®) when treated or coated to provide a granular or fibrous surface, may offer a substrate for tissue in-growth. An alternative form of the in-growth matrix may be an open celled polymeric foam (e.g., PVA foam) in place of a material that must be irradiated to attain the open fibrous or granular nature.

The in-growth surface 106 can also comprise, e.g., woven or knitted Dacron® (PET) fabric placed on a substrate of polydimethylsiloxane (PDMS) or polyurethane (PU); metallic surface structures created by electroform processing; a sintered metal surface (e.g., stainless steel, platinum, iridium, or alloys thereof); parylene coatings; or diffusion limited aggregated silicones. The in-growth surface 106 can also comprise mechanical structures, such as spike, staples, times, coils, or perforations of appropriate dimensions associated with the magnetic implant. The metalic implant may also include compounds to promote coagulation and/or antibiotics to prevent infection, used alone or in combination with the in-growth surface 106.

It may be desirable to mechanically anchor the magnetic implant while allowing in-growth to occur. Temporary anchoring may be accomplished by use of resorbable sutures, screws or other mechanical fasteners made of resorbable materials such as polyglycolic acid or other similar compounds. Tissue adhesives may also be used to provide tissue adhesion, fixation, and stabilization.

a. Temporary Shunt Device

FIG. 17A shows the use of a temporary shunt device 108, which is sized and configured for use during a tissue in-growth period in combination with a magnetic implant MI having an in-growth surface 106 (see FIG. 17B). The shunt device 108 is made of material(s) that are selected to shunt or short a magnetic field produced by an appropriate magnetic force, so that the magnetic implant MI does not shift or move as a result of the magnetic field while tissue in-growth is taking place. For the purpose of illustration, in FIG. 17B, the magnetic implant MI is shown fixed vertically along a pharyngeal wall.

As shown in FIG. 17A, the shunt device 108 comprises one or more soft ferromagnetic alloys 110/112 assembled in layers. The layers 110/112 may comprise, e.g., HYMU-80 material, 2V Permendur material; Hiperco 50A material; Puron material; Stainless Steel 410 or 17-4 material; or 1010 carbon steel material; 3N5 (99.95%) iron material; or any other suitable metal of alloy that has high permeability and/or saturation. These materials may be coated on a substrate.

As shown in FIG. 17A, the shunt device 108 includes two layers 110/112 of soft ferromagnetic alloys. The shunt device 108 is desirably coated with a protective material 58 (as already described) for biocompatibility, corrosion resistance, and durability. The shunt device 108 desirably lends itself for temporary attachment by suturing or stapling to the surface of the target tissue site overlying the magnetic implant MI (as FIG. 17B shows). In FIG. 17A, apertures 114 are provided for this purpose. Alternatively, the shunt device 108 can be implanted and later removed. Still alternatively, the shunt device 108 can be removably attached to the face of the magnetic implant. Desirably, the shunt device 108 (unlike the magnetic implant MI) is surface treated to minimize tissue in-growth. This facilitates removal of the shunt device 108 after tissue in-growth has progressed to a satisfactory degree on the magnetic implant.

The material and construction of the shunt device 108 desirably impart flexibility to avoid interference with normal anatomic function, e.g., swallowing. As FIG. 17C shows, flexibility may be obtained by integrating with the alloy structure segments of materials 116 such as polydimethylsiloxane (PDMS) or polyurethane (PU). Other suitable elastomers, such as Hytrel® material may also be used to impart flexibility. These segment materials 116 also make it possible to match on the shunt device 108 the gross magnetic cross section of the magnetic implant MI.

IV. Illustrative External Ferromagnetic Assemblies Useable with the Magnetic Force System As before described, the source 14 of the magnetic force can comprise a permanent magnet (or electromagnet) implanted in targeted tissue in the pharyngeal conduit, or alternatively, it can comprise a permanent magnet (or electromagnet) implanted or carried external to the pharyngeal conduit. Viable sites for locating an external source for effective magnetic interaction with ferromagnetic materials within the pharyngeal conduit include the oral cavity, the neck, the jaw, the head, and the chin. The system 10 includes a selection of various external appliances worn in the mouth, on the neck, or on the head, from which a practitioner may select to create an external support site for a magnetic force source. Representative examples of these appliances will now be presented. The appliances are desirably worn after a suitable time following implantation of the devices, to allow implant stabilization, tissue in-growth, and healing to occur.

A. Oral Appliances

Appliances worn in the oral cavity can provide an external source of magnetomtive force for interacting with ferromagnetic material implanted in targeted pharyngeal structures and/or anatomic components within the pharyngeal conduit.

1. To Provide an Attracting Magnetic Force

One illustrative arrangement is shown in FIG. 18A. A magnetic force source 14 (e.g., one or more permanent magnets 62) is carried by an oral appliance 118. The oral appliance 118 is sized and configured to be worn on the front lower teeth (see FIG. 18B), desirably during periods of sleep. The permanent magnets can be of any shape, size, composition, and/or orientation. As already explained, an electromagnet can be substituted for a permanent magnet.

The oral appliance 118 is fitted to be worn on the front lower teeth, to hold the position of the source 14 in a stable manner at the front of the oral cavity during sleep. This general configuration of oral appliance is well known to the dental profession for other purposes, and is made for each patient from impressions taken by the dentist. The oral appliance 118 enables full freedom of movement for the lower jaw.

In the embodiment shown in FIG. 18B, the desired physiologic response (resistance of airway tissue collapse) is achieved by the source magnets 62 creating a magnetic field F that interacts with ferromagnetic material 12 implanted in the anterior (front) of the tongue. The implanted ferromagnetic material 12 can comprise permanent magnets having a magnetic orientation opposite to the magnets 62 of the source 14, or a soft ferromagnetic material. The permanent magnets or soft ferromagnetic material can be of any shape, size, composition, and/or orientation. The implanted ferromagnetic material 12 can be of a tethered implant type, shown in FIGS. 13A and 13B, and already described. The magnetic field F between opposite magnetic orientations creates an attracting force. As a result of the attracting force, the tongue is drawn forward, toward the front of the oral cavity, to resist an occlusion of the airway at the base of the tongue.

As FIG. 18C shows, two ferromagnetic implants 12(1) and 12(2) can be provided on opposite lateral sides of the tongue. In this arrangement, the oral appliance 118 carries a corresponding number of permanent magnets 62(1) and 62(2) magnetically aligned with the ferromagnetic implants 12(1) and 12(2). The attracting force is therefore applied simultaneously to left and right front lateral sides of the tongue.

2. To Provide a Repelling Magnetic Force

Another illustrative arrangement is shown in FIG. 19A. A magnetic force source 14 (e.g., one or more permanent magnets 62) is carried by an oral appliance 120 sized and configured to be worn on the lower teeth during periods of sleep (see FIG. 19B). The permanent magnets can be of any shape, size, composition, and/or orientation. As already explained, an electromagnet can be substituted for a permanent magnet 62.

The configuration of the oral appliance 120 shown in FIGS. 19A and 19B is, in general, similar to dental appliances used for prevention of bruxism and snoring. This general type of oral appliance is well known to the dental profession for these purposes and is made for each patient from impressions taken by the dentist. The oral appliance 120 leaves the lower jaw full freedom of movement.

In FIG. 19B, the oral appliance 120 is shown fitted to the lower teeth, which is desirably accomplished prior to going to sleep. The oral appliance 120 holds the magnets 62 of the source 14 at desired positions posterior to the molars. The magnets 62 can be held by the oral appliance 120 either above the lower jaw, or laterally outside the lower jaw, or laterally inside the jaw. Any one or combination of these locations may be utilized.

In the embodiment shown in FIG. 19B, the desired physiologic response (resistance of airway tissue collapse) is achieved by the source 14 creating a magnetic field F that interacts with ferromagnetic material 12 in lateral sides of the pharyngeal wall. The implanted ferromagnetic material 12 can comprise permanent magnets having a magnetic orientation that is the same as the magnetic orientation of the magnets 62 of the source 14. The permanent magnets can be of any shape, size, composition, and/or orientation. The magnetic field between like magnetic orientations generates a repelling force. The repelling force provides resistance against tissue collapse in the pharyngeal conduit, to resist an occlusion of the airway.

B. Neck Appliances

Appliances worn about the neck can also provide an external source of magnetomtive force for interacting with ferromagnetic material implanted in targeted pharyngeal structures and/or anatomic components within the pharyngeal conduit.

FIG. 20A shows an illustrative configuration for a full neck collar 122, which sized and configured to be worn completely about the neck (see FIG. 20B). The collar 122 can be, e.g., of a cloth-covered foam material for comfort and may have a stretch closure strip 124 (as shown in FIG. 20A). Alternatively, the collar 122 can include a hook and loop fastener such as Velcro® material, or simply a buckle or hook and eye means of closure. A fabric preferably covers the collar 122 to enhance the comfort for the wearer. The fabric covering may be, e.g., a terry cloth or jersey type fabric, which can be removable for washing. Further, the collar 122 desirably includes a stiffening member (not shown) that is encased within the foam or on the outer surface of the foam. The stiffening member provides control of the shape of the collar, and have sufficient spring characteristics to allow the collar 122 to be spread slightly open to don and remove the collar 122.

In the embodiment shown in FIG. 20A, the collar 122 may have a curvature that rests behind the jaw bone, to prevent rotation of the collar 122 during sleep. With patients that do not have a clearly defined jaw (such as in obese people), it may be desirable to incorporate an adhesive patch to prevent rotation of the collar 122.

As shown in FIG. 20A, the collar 122 carries a magnetic force source 14, which comprise one or more permanent magnets 62. The permanent magnets can be of any shape, size, composition, and/or orientation.

In the embodiment shown in FIG. 20A, the permanent magnets 62 can be inserted into pockets 126 in the collar. The pockets 126 allow the physician or medical technician to select magnets 62 for type and strength appropriate to the needs of the patient. The pockets 126 also allow the physician to select the placement of the source magnets 62 for interaction with ferromagnetic material 12 implanted in the pharayngeal conduit. The magnets may be single or multiple magnets. Electromagnets may be used in place of permanent magnets.

In the embodiment shown in FIG. 20A, the pockets 126 accommodate the placement of arrays of permanent magnets 62 on the left side of the collar 122, on the right side of the collar 122, and on the front of the collar 122. The physician selects the placement according to the desired physiologic response.

In the embodiment shown in FIG. 20C, the physician inserts arrays of permanent magnets 62 in the left and right side pockets 126 of the collar 122. In this arrangement, the desired physiologic response (resistance of airway tissue collapse) is achieved by the source magnets 62 creating magnetic fields F1 and F2 that interacts with ferromagnetic material 12 implanted in left and right lateral sides of the pharyngeal wall (i.e., the portion of the pharyngeal wall that extends on the left and right sides of the spinal column, which extends generally along the midline of the pharyngeal wall). The implanted ferromagnetic material 12 can be either a soft magnetic material or a permanent magnet. In the case of implanted permanent magnets, the magnets have a magnetic orientation opposite to the magnetic orientation of the magnets 62 of the source 14. The permanent magnets can be of any shape, size, composition, and/or orientation. The magnetic fields F1 and F2 between opposite magnetic orientations create attracting forces between the magnets 62 carried on the collar 122 and the implanted magnets 12. The attracting forces F1 and F2 provides resistance against tissue collapse in the pharyngeal conduit, to resist an occlusion of the airway.

In the embodiment shown in FIG. 20C, the physician also inserts an array of permanent magnets 62 in the front pockets 126 of the collar 122. The permanent magnets can be of any shape, size, composition, and/or orientation.

In this arrangement, a desired physiologic response (resistance of airway tissue collapse) is achieved by the source magnets 62 on the front of the collar 122 creating a magnetic field F3 that interacts with ferromagnetic material 12' implanted in the posterior (base) of the tongue. The source magnets in the collar 122 exert an attracting force on the implanted ferromagnetic material 12', which can be either soft magnetic material or a permanent magnet. In the case of permanent magnets, the magnets have a magnetic orientation opposite to the magnetic orientation of the magnets 62 of the source 14 on the front of the collar 122. The permanent magnets can be of any shape, size, composition, and/or orientation. The implants 12' can be, e.g., a tethered implant type, shown in FIGS. 13A and 13B, and already described.

The magnetic force F3 between opposite magnetic orientations creates an attracting force. As a result of the attracting force F, the tongue is drawn forward, toward the front of the oral cavity, to resist an occlusion of the airway at the base of the tongue.

In the embodiment shown in FIG. 20C, the implanted ferromagnetic materials 12 and 12' in the lateral pharyngeal walls and back of the tongue are permanent magnets, and all possess the same magnetic orientation, which is opposite to the magnetic orientation of the magnets 62 carried by the source collar 122. It is this opposite magnetic orientation that creates the attracting magnetic forces F1, F2, and F3 between the magnets 62 in the collar 122 and the implanted ferromagnetic materials 12 and 12' in the pharyngeal conduit. The same magnetic orientation among the implanted ferromagnetic materials 12 and 12' also creates repelling forces within tissue in the pharyngeal conduit. The repelling forces themselves resist occlusion of the pharyngeal conduit. This dynamic interaction provides a magnetic force to attract (i.e., hold) the implanted ferromagnetic materials 12 and 12' away from the center of the pharyngeal conduit (collar to implants), which aids the repelling forces between the implants themselves (implants to implants). An enhanced physiologic response is created by this dynamic interaction.

The configuration of the collar 122 can vary depending upon the anatomic placement and location of the implanted ferromagnetic materials 12 and 12'. Taking this into account, a given collar need not fully encircle the neck.

For example, a partial neck collar 128 is shown in FIG. 21A. The collar 128 is worn on the side and back of the neck. In this arrangement (see FIG. 21B), the physician inserts arrays of permanent magnets 62 in left and right side pockets 126 of the collar 128, as well as in pockets 126 in the back of the collar 128. In this arrangement, the desired physiologic response (resistance of airway tissue collapse) is achieved by the source magnets 62 creating magnetic fields F1, F2, and F3 that interact with arrays of ferromagnetic materials 12 implanted in left and right lateral sides of the pharyngeal wall. The implanted ferromagnetic materials 12 have a magnetic orientation opposite to the magnetic orientation of the source magnets 62. The magnetic fields F1, F2, and F3 between opposite magnetic orientations create an attracting force between the magnets 62 carried on the collar 128 and the implanted magnets 12. The attracting forces F1, F2, and F3 provide resistance against tissue collapse in the pharyngeal conduit, to resist an occlusion of the airway.

As in the embodiment shown in FIG. 20C, the implanted ferromagnetic materials 12 in the lateral pharyngeal walls all possess the same magnetic orientation. The same magnetic orientation among the implanted ferromagnetic materials 12 also creates repelling forces within tissue in the pharyngeal conduit. The repelling forces themselves resist occlusion of the pharyngeal conduit. As in FIG. 20C, the arrangement shown in FIG. 21B creates a dynamic interaction that provides a magnetic force to attract (i.e., hold) the implanted ferromagnetic material 12s away from the center of the pharyngeal conduit (collar to implants), which aids the repelling forces between the implants themselves (implants to implants).

Yet another illustrative collar is shown in FIGS. 22A and 22B. The collar 130 is sized and configured to conform to the back and sides of the head and neck and to slope downward and outward towards the shoulders. The collar 130 may be constructed of a fabric covered polymeric shape, as previously described. The collar 130 has a chin piece 132. The chin piece 132 is attached to the collar 130 by straps 134. The straps 134 may be elastic or may be adjusted by use of a buckle or hook and loop fastening strip such as Velcro®.

The chin piece 132 carries a magnetic force source 14, which comprise one or more permanent magnets 62. The permanent magnets can be of any shape, size, composition, and/or orientation. As already explained, an electromagnet can be substituted for a permanent magnet.

In this arrangement (see FIG. 22C), the desired physiologic response (resistance of airway tissue collapse) is achieved by the source magnets 62 on the chin piece 132 creating a magnetic field F that interacts with ferromagnetic material 12 implanted in the anterior (front) of the tongue. The implanted ferromagnetic material 12 has a magnetic orientation opposite to the magnetic orientation of the source magnets 62 in the chin piece 132. The implanted ferromagnetic material 12 can be, e.g., a tethered implant type, shown in FIGS. 13A and 13B, and already described. The magnetic force F between opposite magnetic orientations creates an attracting force. As a result of the attracting force F, the tongue is drawn forward, toward the front of the oral cavity, to resist an occlusion of the airway at the base of the tongue.

As FIG. 22B shows, the collar 130 may also carry a magnetic force source 14 on its left and right sides. The force source 14 may comprise one or more permanent magnets 62. The permanent magnets can be of any shape, size, composition, and/or orientation. As already explained, an electromagnet can be substituted for a permanent magnet.

In this arrangement, the desired physiologic response (resistance of airway tissue collapse) is achieved by the source magnets 62 on the left and right sides of the collar 130 creating a magnetic field that interacts with arrays of ferromagnetic material 12 implanted in left and right lateral sides of the pharyngeal wall (e.g., in the pattern shown in FIG. 20C). The implanted ferromagnetic materials 12 can comprise permanent magnets having a magnetic orientation opposite to the magnetic orientation of the source magnets 62 or a soft ferromagnetic material. The permanent magnets can be of any shape, size, composition, and/or orientation. The magnetic field between opposite magnetic orientations creates an attracting force between the magnets carried on the side of the collar 130 and the implanted ferromagnetic material 12. The attracting force provides resistance against tissue collapse in the pharyngeal conduit, to resist an occlusion of the airway. Due to the design of the collar 130 shown in FIGS. 22A and 22B, the collar 130 can accommodate either a larger or a greater quantity of magnets 62 on the side of the collar 130. This arrangement makes possible the delivery of a greater magnetic force than previous configurations shown in FIGS. 20A and 21.

The advantages of external neck appliances include: (1) Larger and stronger magnets may be used than could be either implanted or affixed to an appliance worn in the mouth; (2) The force delivered will only be experienced when the patient wishes to sleep and no effect on eating or speech would be experienced; and (3) Without need for surgical intervention, the amount and direction of the magnetic forces can be changed. This is accomplished by exchanging magnet types and sizes and by changing the location of the magnets within the collars and chin pieces.

It should be appreciated that discrete permanent magnets or arrays of permanent magnets may be attached to the side of the neck without use of an appliance. Discrete magnets or arrays of magnets may be affixed with adhesives or tapes on external skin surfaces of the neck, chin, head, or jaw to achieve comparable interaction with implanted ferromagnetic materials.

C. Head-Worn Appliances

Appliances worn on the head can also provide an external source 14 of magnetic force for interacting with ferromagnetic material 12 implanted in targeted pharyngeal structures and/or anatomic components within the pharyngeal conduit.

FIG. 23A shows an illustrative configuration for a head-worn appliance 136. The appliance 136 comprises a molded headgear that conforms to the top of the head with left and right sidepieces that fit over the ears, like a headphone. The sidepieces extend below the ears, providing an area for carrying a magnetic force source 14 on its left and right sides. The force source 14 may comprise one or more permanent magnets 62. The permanent magnets can be of any shape, size, composition, and/or orientation. As already explained, an electromagnet can be substituted for a permanent magnet.

In this arrangement, the desired physiologic response (resistance of airway tissue collapse) is achieved by the source magnets 62 on the left and right sides of the head appliance 136 creating a magnetic field that interacts with ferromagnetic material 12 implanted in left and right lateral sides of the pharyngeal wall (e.g., in the pattern shown in FIG. 20C), as already described.

FIG. 23B shows another illustrative embodiment of a head-worn appliance 138. The appliance 138 includes a molded headgear that wraps around the head and includes an elastic strap that extends over the ears and supports a chin cup 140. The chin cup 140 carries a magnetic force source 14. The force source 14 may comprise one or more permanent magnets 62. The permanent magnets can be of any shape, size, composition, and/or orientation. As already explained, an electromagnet can be substituted for a permanent magnet.

In this arrangement, the desired physiologic response (resistance of airway tissue collapse) is achieved by the source magnets 62 on the chin cup 140 creating a magnetic field that interacts with ferromagnetic material implanted in the tongue (e.g., in the pattern shown in FIG. 22C), as already described.

FIG. 23C shows another illustrative embodiment of a head-worn appliance 142. The appliance 142 includes a molded headgear comprising a helmet having pouches or cups 144 for carrying a magnetic force source 14. The force source 14 may comprise one or more permanent magnets 62. The permanent magnets can be of any shape, size, composition, and/or orientation. As already explained, an electromagnet can be substituted for a permanent magnet.

In this arrangement, the desired physiologic response (resistance of airway tissue collapse) is achieved by the source magnets 62 on the left and right sides of the head appliance 142 creating a magnetic field that interacts with ferromagnetic material 12 implanted in left and right lateral sides of the pharyngeal wall (e.g., in the pattern shown in FIG. 20C), as already described.

It can be seen that the same sort of headgear with only slight modification could provide a means of holding magnets at any location on the neck, cheek, lips, etc.

V. Orienting Multiple Sources of Magnetism

As described above, the system 10 includes at least one ferromagnetic material 12 implanted in a targeted tissue region within targeted pharyngeal structures and individual anatomic components in the pharyngeal conduit. As also described above, the ferromagnetic material 12 can comprise a discrete source of magnetism, or multiple sources of magnetism, each having the same magnetic orientation, arranged in close proximity to each other. The magnets can be of any shape, size, composition, and/or orientation.

The orientation of the multiple sources of magnetism, once implanted, can vary according to the particular anatomy of the targeted tissue region and its environs, which govern the mechanism by which the desired physiologic response is achieved.

A. Horizontal Orientation

For example, the particular anatomy and tissue mass of the targeted tissue region may lend itself to the implantation of multiple sources of magnetism in a generally horizontal plane. With respect to anatomic landmarks, horizontal arrays extend either laterally (from side to side) or anterior-to-posterior (front to back), following the natural morphology of the tissue.

For example (see FIG. 24A), the anatomy and the tissue mass of the tongue accommodates implantation of a horizontal array of multiple sources of magnetism 146 (e.g., each one comprising a permanent magnet or ferromagnetic material) either laterally in the base of the tongue, or anterior-to-posterior along one or both sides of the tongue, or both. The flexible magnetic arrays or coiled arrays previously described lend themselves to either arrangement. As FIG. 24B shows, horizontal arrays of multiple sources of magnetism 146, each having the same magnetic orientation, can be implanted in stacked or staggered fashion on the posterior of the tongue, at different elevations along the pharyngeal conduit.

As another example (see FIG. 25A), the anatomy and the tissue mass of the lateral pharyngeal wall accommodates implantation of a horizontal array of multiple sources of magnetism 146 (e.g., each one comprising a permanent magnet or ferromagnetic material) following the morphology of the posterior and lateral walls of the larynx on opposite lateral sides of the spinal column. In the pharyngeal wall, the horizontal array may be discontinuous (FIG. 25A) or continuous (FIG. 25B), forming a continuous array following the circumferential morphology of the pharyngeal wall that extends posterior from the spinal column to the base of the tongue. Discrete magnets, the flexible magnetic arrays, or coiled arrays previously described lend themselves to either arrangement.

Figure 25A:
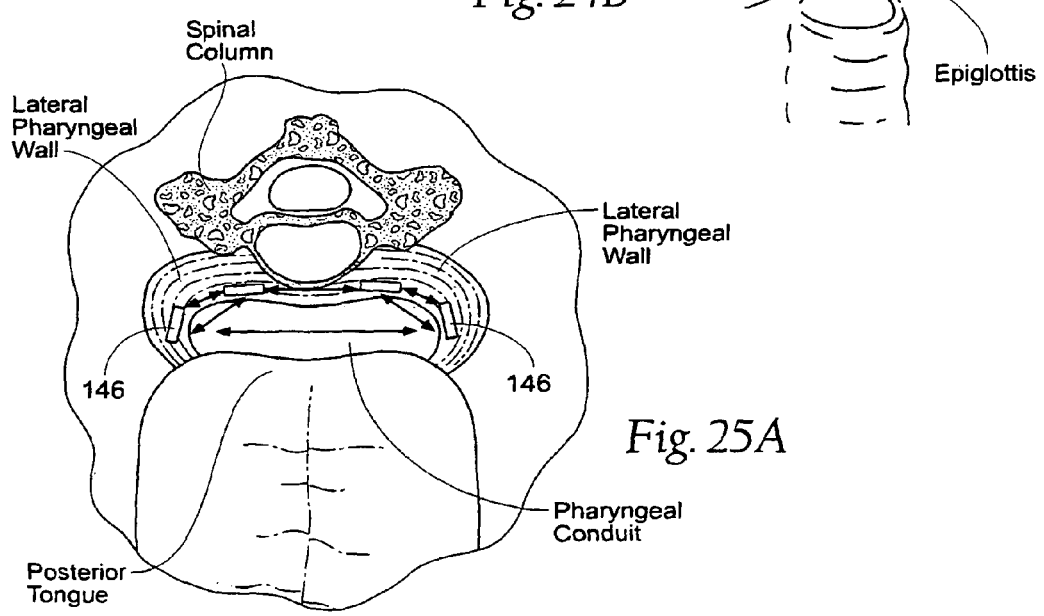
Figure 25B:
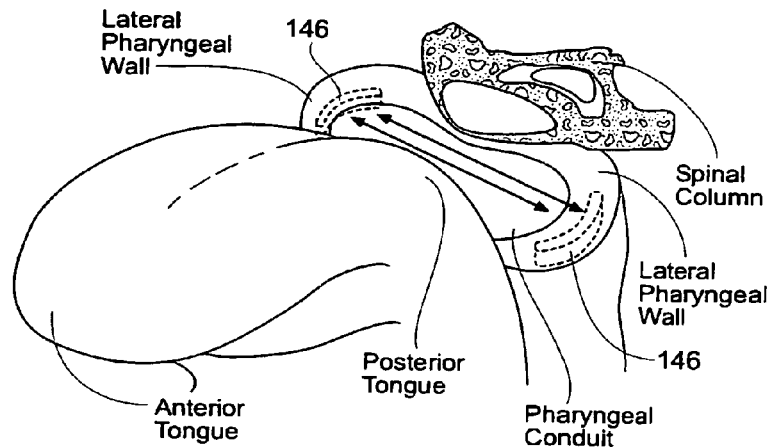
Figure 25C:
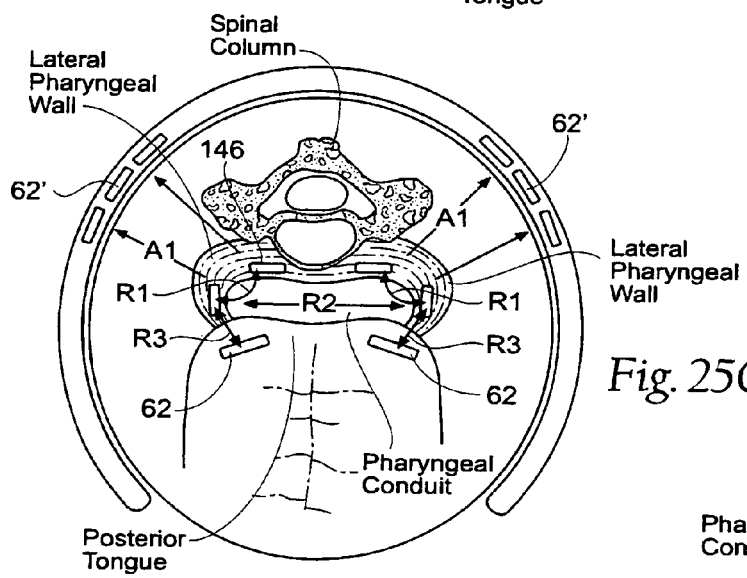
Figure 25D:
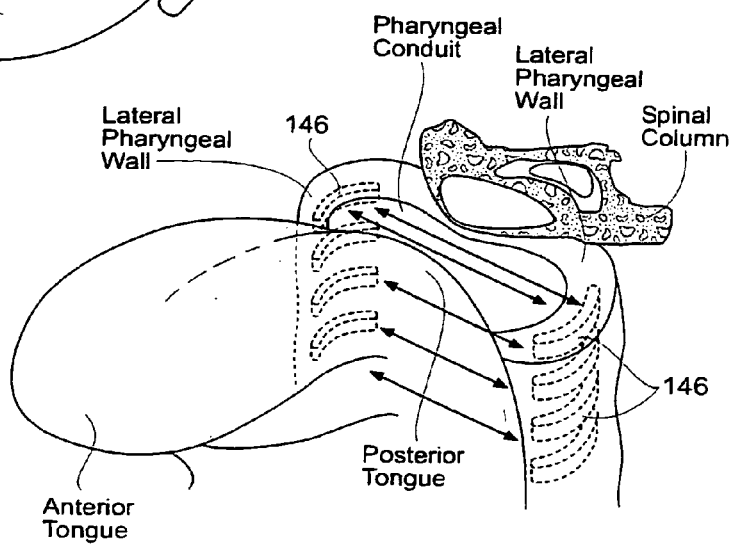

As FIG. 25D shows, horizontal arrays of multiple sources of magnetism 146, each having the same magnetic orientation, can be implanted in stacked or staggered fashion within the lateral pharyngeal wall. The arrays 146 may be discontinuous or form concentric bands about the pharyngeal wall at different elevations along the pharyngeal conduit.

The placement of horizontal arrays of permanent magnets, each having the same magnetic orientation, within the lateral pharyngeal wall creates dynamic interactions of repelling magnetic forces. As shown in FIG. 25C, a first repelling force (shown by double headed arrows R1) exists between magnets in the array 146 that face across the pharyngeal conduit on the same lateral side of the pharyngeal wall. A second repelling force (shown by double headed arrows R2) exists between magnets that face across the pharyngeal conduit on opposite lateral sides of the pharyngeal wall. These dynamic repelling forces serve to resist collapse of tissue within the pharyngeal conduit and facilitate the desired physiologic result.

In the presence of another permanent magnet 62 or magnets having the same magnetic orientation implanted, e.g., in the base of the tongue (as FIG. 25C shows), yet a third repelling force (shown by double head arrow R3) exists between magnets that face across the pharyngeal conduit in an anterior-to-posterior orientation. These dynamic repelling forces further serve to resist collapse of tissue within the pharyngeal conduit and further facilitate the desired physiologic result. Other permanent magnet or magnets can be implanted across from the posterior wall at other elevations along the pharyngeal conduit to achieve the same anterior-to-posterior repelling force and desired physiologic response, e.g., in the soft palate, epiglottis, or vallecula.

In the presence of an external permanent magnet 62' or magnets having an opposite magnetic orientation positioned laterally (and, optionally, posteriorly) to the magnets in the pharyngeal wall, an attracting force (shown by single headed arrow A1) exists between the external magnet or magnets and the magnets in the pharyngeal wall. This arrangement has already been generally discussed with respect to FIG. 20C. This dynamic interaction between repelling and attracting forces serves to resist collapse of tissue within the pharyngeal conduit and further facilitate the desired physiologic result.

B. Vertical Orientation

The particular anatomy and tissue mass of the targeted tissue region may lend itself to the implantation of multiple sources of magnetism 146 in a generally vertical plane. With respect to anatomic landmarks, vertical arrays extend in a superior (cephalad)-to-inferior (caudal) direction, following the natural morphology of the tissue mass.

For example (see FIG. 26A), the anatomy and the tissue mass of the pharyngeal wall accommodates implantation of a vertical array of multiple sources of magnetism 146 (e.g., each one comprising a permanent magnet or ferromagnetic material)—following the morphology of opposite lateral pharyngeal walls. Discrete magents, the magnetic strip arrays, or coiled arrays previously described lend themselves to either arrangement.

As FIG. 26B shows, vertical arrays of multiple sources of magnetism 146, each having the same magnetic orientation, can be implanted either end-to-end or side-by side within the lateral pharyngeal wall.

As with the placement of horizontal arrays of permanent magnets, each having the same magnetic orientation, within the lateral pharyngeal wall, the placement of vertical arrays of permanent magnets, each having the same magnetic orientation, can create dynamic interactions of repelling magnetic forces. As shown in FIG. 26C, a first repelling force (shown by double headed arrows R1) exists between magnets in the array that face across the pharyngeal conduit on the same lateral side of the pharyngeal wall. A second repelling force (shown by double headed arrows R2) exists between magnets that face across the pharyngeal conduit on opposite lateral sides of the pharyngeal wall. These dynamic repelling forces serve to resist collapse of tissue within the pharyngeal conduit and facilitate the desired physiologic result.

In the presence of another permanent magnet 62 or magnets having the same magnetic orientation implanted, e.g., in the base of the tongue, yet a third repelling force (shown by double head arrow R3) exists between magnets that face across the pharyngeal conduit in an anterior-to-posterior orientation. These dynamic repelling forces serve to resist collapse of tissue within the pharyngeal conduit and further facilitate the desired physiologic result. Other permanent magnet or magnets can be implanted across from the posterior wall at other elevations along the pharyngeal conduit to achieve the same anterior-to-posterior repelling force, e.g., in the soft palate, epiglottis, or vallecula.

In the presence of an external permanent magnet 62' or magnets having an opposite magnetic orientation positioned laterally (and, optionally, posterior) to the magnets in the pharyngeal wall, an attracting force (shown by single headed arrow A1) exists between the external magnet or magnets and the magnets in the pharyngeal wall. The dynamic interaction between repelling and attracting forces serve to resist collapse of tissue within the pharyngeal conduit and further facilitate the desired physiologic result.

C. Other Orientations

The particular anatomy and tissue mass of the targeted tissue region may lend itself to the implantation of multiple sources of magnetism 146 in both a generally horizontal plane and a generally vertical plane.

For example (see FIG. 27A), the anatomy and the tissue mass of the pharyngeal wall accommodates implantation of vertical arrays of multiple sources of magnetism 146, each having the same magnetic orientation, with horizontal arrays of multiple sources of magnetism 146, each having the same magnetic orientation, along the elevation of the pharyngeal conduit. This complex implantation pattern makes possible the formation of dynamic repelling forces that facilitate the physiologic objective of resisting tissue collapse along the pharyngeal conduit.

The particular anatomy and tissue mass of the targeted tissue region may lend itself to the implantation of multiple sources of magnetism 146 in angular planes (i.e., not horizontal or not vertical planes).

For example (see FIG. 27B), the anatomy and the tissue mass of the pharyngeal wall accommodates implantation of angular, non-horizontal and non-vertical arrays of multiple sources of magnetism 146, each having the same magnetic orientation. This complex implantation pattern makes possible the formation of dynamic repelling forces that facilitate the physiologic objective of resisting tissue collapse along the pharyngeal conduit.

VI. Illustrative Systems

Based upon the foregoing discussions, a practitioner can select and assemble components in various ways to create systems 10 of different configurations to achieve the desired physiologic response. Generally, the systems 10 can be placed into three general categories:

(1) Systems 10 that include ferromagnetic material or materials that are implanted in targeted pharyngeal structures and individual anatomic components in the pharyngeal conduit, which interact with source or sources of magnetic forces that are also implanted in targeted pharyngeal structures and individual anatomic components in the pharyngeal conduit. This category of systems 10 relies upon repelling force to achieve the desired physiologic response.

(2) Systems 10 that include ferromagnetic material or materials that are implanted in targeted pharyngeal structures and individual anatomic components in the pharyngeal conduit, which interact with source or sources of magnetic forces that are external to the pharyngeal conduit. This category of systems 10 can rely upon either attracting or repelling forces to achieve the desired physiologic response.

(3) Systems 10 that include ferromagnetic material or materials that are implanted in targeted pharyngeal structures and individual anatomic components in the pharyngeal conduit, which interact with source or sources of magnetic forces, some of which are external to the pharyngeal conduit, and some of which are implanted in targeted pharyngeal structures and individual anatomic components in the pharyngeal conduit.

A. System Category 1 (Implant-Implant)

1. Implants Within the Pharyngeal Wall

FIGS. 28A, 28B, 28C, and 28D show illustrative embodiments of one type of system 10 in Category (1). The system 10 includes an array of ferromagnetic materials that are implanted in a vertical array on opposite lateral sides of the pharyngeal wall. As illustrated (see FIGS. 28A and 28B, the ferromagnetic materials comprise a flexible magnetic array 60 of permanent magnets arranged vertically, as previously described (see, e.g., FIG. 26A). The permanent magnets can be of any shape, size, composition, and/or orientation. The source of magnetic forces comprises an array 60 of permanent magnets having the same magnetic orientation, implanted in the opposite wall of the pharyngeal conduit (i.e., the posterior tissue of the tongue). As illustrated, the array comprises another flexible magnetic array 60 of permanent magnets having the same magnetic orientation. The permanent magnets can be of any shape, size, composition, and/or orientation. It should be appreciated that stacked horizontal arrays, or a combination of horizontal and vertical arrays, or angular arrays could be used. The arrays interact with repelling forces that resist collapse of tissue along the pharyngeal conduit.

Magnets may be arranged on opposite sides of the pharyngeal conduit in uneven opposing numbers.

Figure 28A:
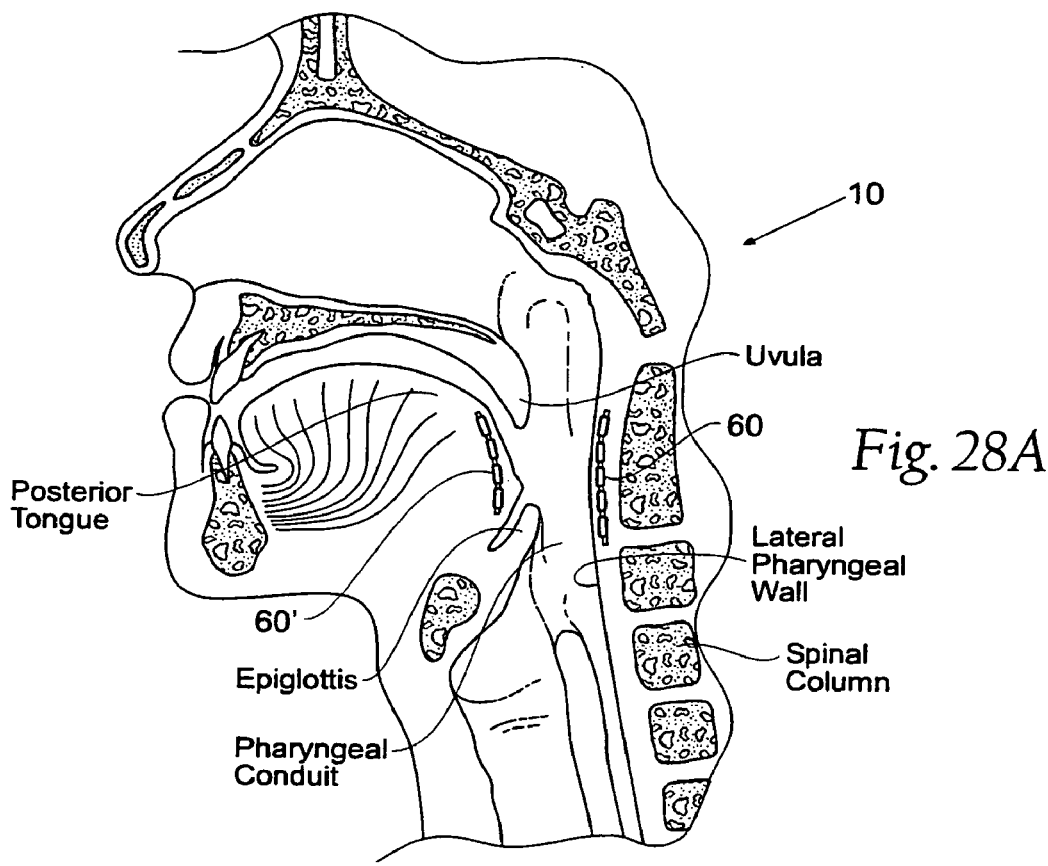
Figure 28B:
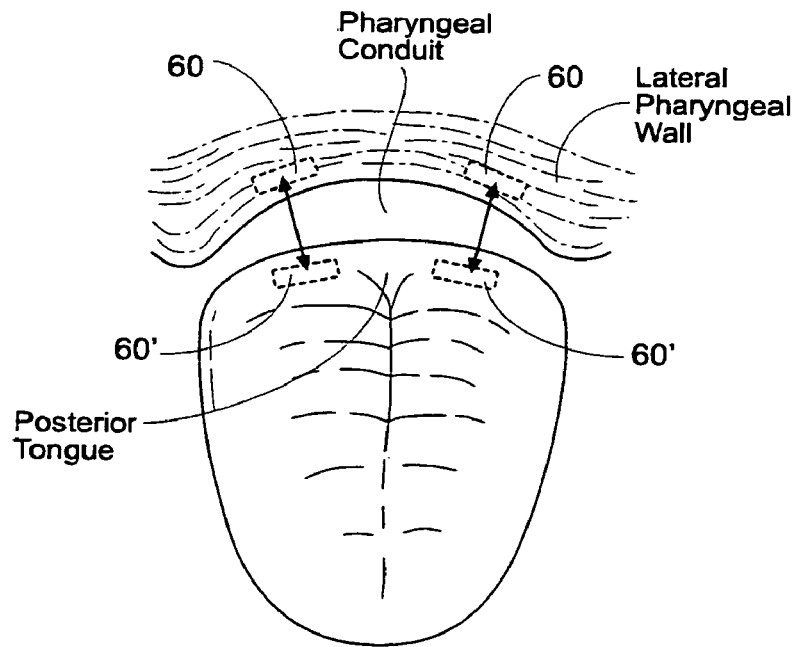
Figure 28C:
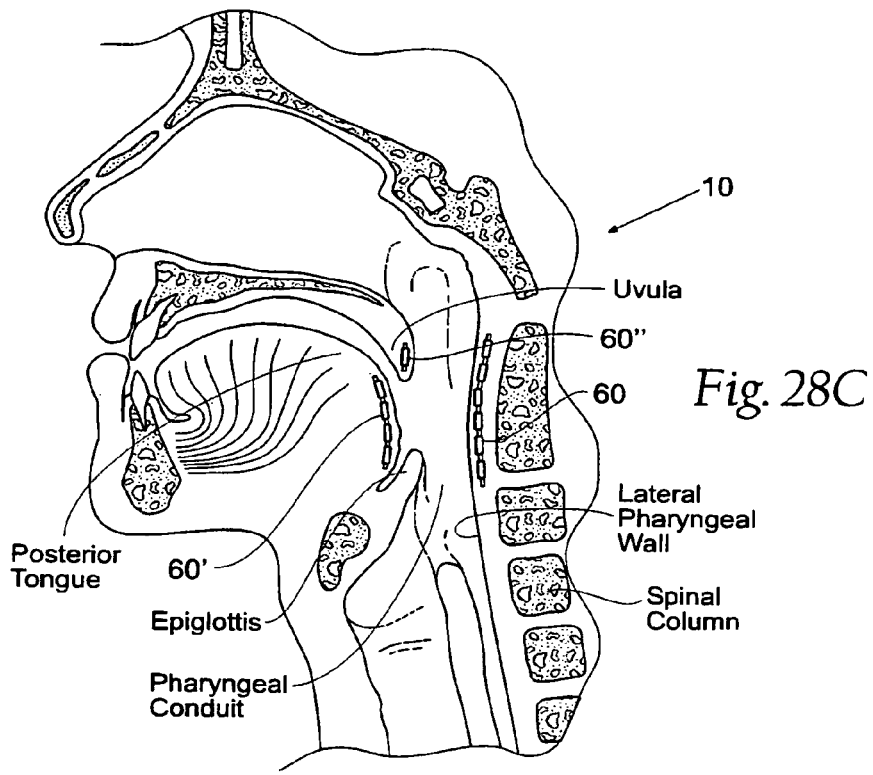
Figure 28D:
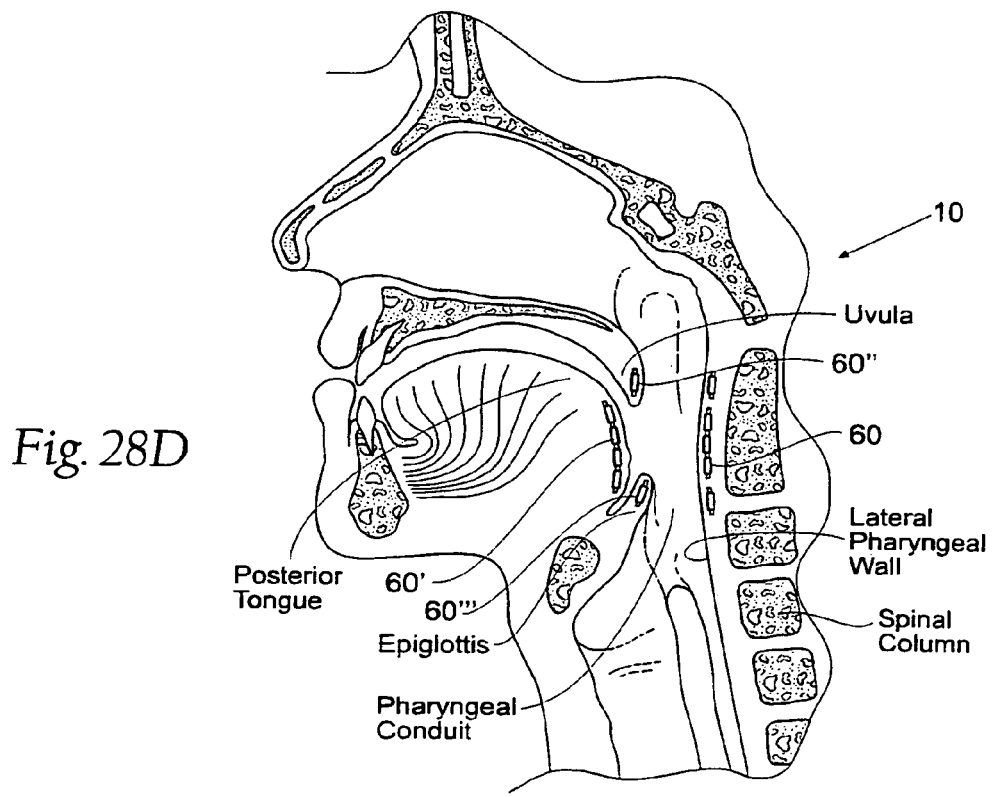

FIG. 28C shows a variant of the system 10, in which the magnet arrays 60 in the lateral pharyngeal walls extend superiorly (toward the head) and interact (with repelling forces) with one or more magnets 60" having the same magnetic orientation implanted in the uvula and/or soft palate. FIG. 28D shows a further variant of the system 10, in which the magnet arrays 60 in the lateral pharyngeal walls extend inferiorly (toward the feet) and interact (with repelling forces) with one or more magnets 60''' having the same magnetic orientation implanted in the epiglottis. As FIG. 28D shows, the magnetic arrays implanted in the lateral pharyngeal wall may be continuous or comprise a series of shorter (e.g., 1 to 2 cm) lengths, or individual (discrete) magnets.

2. Implants Within the Tongue

FIG. 29 shows an illustrative embodiment of another type of system 10 in Category (1). The system 10 includes ferromagnetic materials 62 that are implanted on opposite lateral sides in the base of tongue. As illustrated, the ferromagnetic materials magnets can comprise permanent magnets. The permanent magnets can be of any shape, size, composition, and/or orientation. The source of magnetic forces comprises permanent magnets 62' having the same magnetic orientation, implanted in the opposite lateral sides in the soft palate. The permanent magnets can be of any shape, size, composition, and/or orientation. The opposed permanent magnets interact with repelling forces that push the tongue forward to resist collapse of tissue along the pharyngeal conduit.

B. System Category 2 (Implant to External)

1. Attracting Forces

FIGS. 18B and 18C (previously described) show an illustrative embodiment of a type of system 10 in Category (2). The system 10 includes ferromagnetic material or materials that are implanted in a targeted anatomic component in the pharyngeal conduit. In FIGS. 18B and 18C, the ferromagnetic material comprises one or more permanent magnets, or soft ferromagnetic material. The permanent magnets or soft ferromagnetic material can be of any shape, size, composition, and/or orientation. The magnets are implanted in the anterior (front) tongue. The implanted permanent magnets interact with source or sources of magnetic forces that are external to the pharyngeal conduit. This source comprises a permanent magnet having a magnetic orientation opposite to the magnetic orientation of the implanted radial magnet. The permanent magnets can be of any shape, size, composition, and/or orientation. The source magnet can comprise a discrete magnet affixed to surface tissue on the neck, chin, jaw, or head; or a magnet carried on an oral appliance that fits on the front teeth, or on an appliance that fits on the neck or head. The interaction creates attracting forces, drawing the tongue forward, to achieve the desired physiologic response.

2. Repelling Forces

FIG. 19B (previously described) show an illustrative embodiment of another type of system 10 in Category (2). The system 10 includes ferromagnetic material or materials that are implanted in a targeted anatomic component in the pharyngeal conduit. In FIG. 19B, the ferromagnetic material comprises one or more permanent magnets. The permanent magnets can be of any shape, size, composition, and/or orientation. The magnets are implanted in lateral pharyngeal walls. The implanted permanent magnets interact with source or sources of magnetic forces that are external to the pharyngeal conduit. In this source comprises a permanent magnet having a magnetic orientation that is the same as the magnetic orientation of the implanted radial magnet. The permanent magnet can be of any shape, size, composition, and/or orientation. The source magnet is carried on an oral appliance that fits on the teeth, to locate the source magnet posterior to the molars. The interaction creates repelling forces, resisting collapse of the pharyngeal conduit, to achieve the desired physiologic response.

C. System Category (3):(Implant-Implant/External)

FIG. 20B (previously described) shows an illustrative embodiment of a type of system 10 in Category (3). The system 10 includes ferromagnetic material or materials that are implanted in targeted pharyngeal structures and individual anatomic components in the pharyngeal conduit. In FIG. 20B, the ferromagnetic material includes horizontal arrays of permanent magnets. The permanent magnets can be of any shape, size, composition, and/or orientation. The array of magnets is implanted on opposite lateral pharyngeal walls.

The implanted array of magnets interacts with two sources magnetic forces. The first source is external to the pharyngeal conduit. In FIG. 20B, the external source comprises a neck-worn collar carrying an array of permanent magnets having an orientation opposite to the orientation of the implanted magnets. The permanent magnets can be of any shape, size, composition, and/or orientation. The second source is implanted in targeted pharyngeal structures and individual anatomic components in the pharyngeal conduit. In FIG. 20B, the second source comprises permanent magnets implanted on lateral sides of the base of the tongue. The permanent magnets can be of any shape, size, composition, and/or orientation. The second source has a magnetic orientation that is the same as the orientation of the implanted magnets.

The interaction with the first source creates attracting forces between the magnets in the pharyngeal wall (and tongue) and the external magnets. The interaction with the second source creates repelling forces between magnets in the pharyngeal wall and the tongue.

This dynamic interaction provides a magnetic force to attract (i.e., hold) the implanted ferromagnetic material 12s away from the center of the pharyngeal conduit (collar to implants), aiding the repelling forces between the implants themselves (implants to implants). An enhanced physiologic response is created by this dynamic interaction, as has been previously described.

Systems 10 of the type belonging to Category (3) have also been previously described with reference to FIGS. 25C and 26C.

VII. Implantation of Magnetic Implants

Magnetic implants of the type described can be implanted in tissue in the pharyngeal conduit in various ways. For example, access for the implant can be achieved through the tonsil fossa.

In a representative procedure for implanting a pharyngeal wall magnetic implant or other pharyngeal wall device: (1) a patient is positioned in the Rose position (supine, neck extended), and a Crowe-Davis (or similar) mouth retractor is placed. The anatomic position of the palatine tonsil is shown in FIG. 32A. The palatine tonsil sits within the tonsil fossa. The tonsil fossa is a recess in the lateral pharyngeal wall bordered by the anterior and posterior tonsil pillars (front and back, respectively), and pharyngeal wall muscle laterally; (2) the palatine tonsils can be surgically removed, leaving the anterior and posterior pillar tissue intact. If tonsils have been previously removed, the healed tonsil fossa is re-opened, conserving existing pillar tissue; (3) an incision is made and a submucosal tunnel is then developed using blunt dissection, beginning along the posterior tonsil pillar/tonsil fossa junction (see FIG. 32B). The tunnel is started either high (closer to the superior fossa) or low (closer to the inferior fossa) depending on the planned position of the implant. The tunnel is dissected inferiorly to a location approximately adjacent to the inferior aspect of the epiglottis. The tunnel can be specifically made narrow or it can be wide by dissecting further anterior or posterior toward midline, depending on implant configuration. The implant (shown in FIG. 32B to be a flexible magnet array 60) is inserted through the incision into the tunnel (see FIG. 32C); (4) an alternative to the above tunneling procedure is the use of a trocar type of implantation device. The device would be placed in a similar fashion (junction of tonsil fossa and posterior pillar) into the submucosal space to be implanted, and the implant would be positioned and then released from the implantation device. The trocar would then be withdrawn; (5) the approach described in (3) and (4) above, can also be extended for placement of implants into the vallecula. In this circumstance, the tunnel would be continued submucosally in a medial direction into vallecula; (6) with the implant in position, 3-0 absorbable sutures may be placed transmucosally through the inferior, mid, and superior aspects of the implant for initial stabilization. The entry site for the tunnel is sutured closed. A deep muscle layer closure within the tonsil fossa is then performed and the fossa is sutured closed (posterior pillar sutured to anterior pillar tissue) with absorbable suture, completing the implantation procedure.

An alternate entry point for submucosal implant placement can be any incision along the pharyngeal wall rather than through the tonsil fossa. Surgical tunneling or trochar placement would then follow as described above. Other upper airway surgery (such as uvulopalatopharyngoplasty) can then be concurrently undertaken, if indicated.

The procedure described above is applicable for the implantation of any pharyngeal wall device. These would include active and passive stabilizing, stiffening or reshaping implantable devices.

The above-described embodiments of this invention are merely descriptive of its principles and are not to be limited. The scope of this invention instead shall be determined from the scope of the following claims, including their equivalents.

What is claimed is:

1. A system comprising a first magnetically interactive material sized and configured for placement in or on a tongue, and a second magnetically interactive material sized and configured for placement in a desired relationship with the tongue to magnetically interact with the first magnetically interactive material by repelling the first magnetically interactive material to stabilize a preferred orientation of the tongue, wherein at least one of the first and second magnetically interactive materials includes at least one source of magnetism having a periphery and a flexible polymer matrix including a protective material encapsulating the at least one source of magnetism, the flexible polymer matrix including an edge region extending beyond the periphery of the source of magnetism to allow flexure of the flexible polymer matrix relative to the source of magnetism.

2. A method comprising placing a first magnetically interactive material in or on a tongue, and placing a second magnetically interactive material in a desired relationship with the tongue to magnetically interact with the first magnetically interactive material by repelling the first magnetically interactive material, stabilizing a preferred orientation of the tongue by the magnetic interaction.

3. A method according to claim 2 wherein the second magnetically interactive material is placed in an airway.

4. A method according to claim 2 wherein the second magnetically interactive material is implanted in tissue in an airway.

5. A method according to claim 2 wherein the second magnetically interactive material is placed in or on a soft tissue region defining a portion of a pharyngeal conduit or a pharyngeal wall or combinations thereof.

6. A method according to claim 2 wherein the second magnetically interactive material is implanted in a soft tissue region defining a portion of a pharyngeal conduit or a pharyngeal wall or combinations thereof.

7. A method according to claim 2 wherein first magnetically interactive material is implanted within tongue tissue.

8. A method according to claim 7 wherein the second magnetically interactive material is implanted in tissue in an airway.

9. A method according to claim 8 wherein the second magnetically interactive material is implanted in a soft tissue region defining a portion of a pharyngeal conduit or a pharyngeal wall or combinations thereof.

10. A method according to claim 2 wherein first magnetically interactive material is implanted within tongue tissue in a posterior region of the tongue.

11. A method according to claim 2 wherein the first magnetically interactive material is implanted entirely within tongue tissue.

* * * * *